(12) United States Patent
Kalghatgi et al.

(10) Patent No.: US 11,724,078 B2
(45) Date of Patent: Aug. 15, 2023

(54) METHODS AND SYSTEMS FOR TRANS-TISSUE SUBSTANCE DELIVERY USING PLASMAPORATION

(71) Applicant: GOJO INDUSTRIES, INC., Akron, OH (US)

(72) Inventors: Sameer Kalghatgi, Copley, OH (US); Abhishek Juluri, Akron, OH (US); Jeffrey S. Louis, Akron, OH (US); Tsung-Chan Tsai, Worthington, OH (US)

(73) Assignee: GOJO Industries, Inc., Akron, OH (US)

( * ) Notice: Subject to any disclaimer, the term of this patent is extended or adjusted under 35 U.S.C. 154(b) by 511 days.

(21) Appl. No.: 17/014,228

(22) Filed: Sep. 8, 2020

(65) Prior Publication Data
US 2020/0406016 A1    Dec. 31, 2020

Related U.S. Application Data

(62) Division of application No. 15/592,568, filed on May 11, 2017, now Pat. No. 10,765,850.
(Continued)

(51) Int. Cl.
*A61M 37/00* (2006.01)
*A61B 18/04* (2006.01)
(Continued)

(52) U.S. Cl.
CPC ....... *A61M 37/0015* (2013.01); *A61B 18/042* (2013.01); *A61K 9/0021* (2013.01);
(Continued)

(58) Field of Classification Search
CPC .. A61M 2037/0007; A61M 2037/0023; A61M 37/0015; A61B 18/042; A61N 1/327; A61N 1/44
See application file for complete search history.

(56) References Cited

U.S. PATENT DOCUMENTS 7,330,755 B2   2/2008   Viöl et al.
7,402,435 B2   7/2008   Miyoshi et al.
(Continued)

FOREIGN PATENT DOCUMENTS

DE   102011001416 A1   9/2012
EP        2016809 A2   1/2009
(Continued)

OTHER PUBLICATIONS

Choi-Jeong-Hae et al., "Treatment with low-temperature atmospheric pressure plasma enhances cutaneous delivery of epidermal growth factor by regulating E-cadherin-medicated cell junctions", Arch Dermatol (2014) 306:635-643.
(Continued)

*Primary Examiner* — Quynh-Nhu H. Vu
(74) *Attorney, Agent, or Firm* — Calfee, Halter & Griswold LLP

(57) ABSTRACT

Exemplary systems and methods associated with trans-tissue substance delivery using non-thermal plasma to porate skin or tissues using contoured dielectrics/electrodes and grounding techniques. In some embodiments, a substance delivery system may be incorporated into the plasma generating device for automatically controlled skin treatments. In other embodiments, a skin treatment patch may include the electrode and the treatment substance.

19 Claims, 23 Drawing Sheets

Related U.S. Application Data

(60) Provisional application No. 62/335,323, filed on May 12, 2016.

(51) Int. Cl.
  *A61N 1/32* (2006.01)
  *A61N 1/44* (2006.01)
  *A61K 9/00* (2006.01)
  A61K 9/70 (2006.01)

(52) U.S. Cl.
  CPC .............. *A61N 1/327* (2013.01); *A61N 1/44* (2013.01); *A61K 9/7084* (2013.01); *A61M 2037/0007* (2013.01); *A61M 2037/0023* (2013.01)

(56) References Cited

U.S. PATENT DOCUMENTS

| | | |
|---|---|---|
| 7,608,839 B2 | 10/2009 | Coulombe et al. |
| 7,633,231 B2 | 12/2009 | Watson |
| 7,683,342 B2 | 3/2010 | Morfill et al. |
| 7,923,251 B2 | 4/2011 | Vankov et al. |
| 3,005,548 A1 | 8/2011 | Watson |
| 8,103,340 B2 | 1/2012 | Viöl |
| 8,283,171 B2 | 10/2012 | Vankov et al. |
| 8,377,388 B2 | 2/2013 | Konesky |
| 8,388,618 B2 | 3/2013 | Fridman et al. |
| 8,455,228 B2 | 6/2013 | Jaroszeski et al. |
| 8,460,283 B1 | 6/2013 | Laroussi et al. |
| 8,521,274 B2 | 8/2013 | Gutsol et al. |
| 8,557,187 B2 | 10/2013 | Ehlbeck et al. |
| 8,725,248 B2 | 5/2014 | Gutsol et al. |
| 8,802,022 B2 | 8/2014 | Konesky |
| 8,810,134 B2 | 8/2014 | Watson |
| 8,828,326 B2 | 9/2014 | Holbeche |
| 8,894,644 B2 | 11/2014 | Stieber et al. |
| 8,900,521 B2 | 12/2014 | Hancock |
| 8,906,659 B2 | 12/2014 | Clyne et al. |
| 8,926,920 B2 | 1/2015 | Morfill et al. |
| 8,928,230 B2 | 1/2015 | Watson et al. |
| 8,957,572 B2 | 2/2015 | Eden et al. |
| 8,992,518 B2 | 3/2015 | Fridman et al. |
| 8,994,271 B2 | 3/2015 | Kindel et al. |
| 9,005,188 B2 | 4/2015 | Wandke et al. |
| 9,006,976 B2 | 4/2015 | Watson et al. |
| 9,038,645 B2 | 5/2015 | Wandke et al. |
| 9,072,157 B2 | 6/2015 | Holbeche et al. |
| 9,192,776 B2 | 11/2015 | Hummel et al. |
| 9,226,790 B2 * | 1/2016 | Zemel ................ H05H 1/2418 |
| 9,236,227 B2 | 1/2016 | Watson et al. |
| 9,257,264 B2 | 2/2016 | Hummel et al. |
| 9,287,094 B2 | 3/2016 | Trutwig et al. |
| 9,295,535 B2 | 3/2016 | Holbeche et al. |
| 9,308,285 B2 | 4/2016 | Hancock et al. |
| 9,330,890 B2 | 5/2016 | Busse et al. |
| 9,339,783 B2 | 5/2016 | Fridman et al. |
| 9,345,120 B2 | 5/2016 | Wandke et al. |
| 9,351,790 B2 | 5/2016 | Zemel et al. |
| 9,384,947 B2 | 7/2016 | Watson et al. |
| 9,387,369 B2 | 7/2016 | Yamamoto |
| 9,418,820 B2 | 8/2016 | Watson et al. |
| 9,437,401 B2 | 9/2016 | Watson et al. |
| 9,440,057 B2 | 9/2016 | Jacofsky et al. |
| 9,472,382 B2 | 10/2016 | Jacofsky |
| 9,498,637 B2 | 11/2016 | Sanders et al. |
| 9,511,240 B2 | 12/2016 | Dobrynin et al. |
| 9,521,736 B2 | 12/2016 | Jacofsky et al. |
| 9,538,630 B2 | 1/2017 | Watson |
| 9,558,918 B2 | 1/2017 | Watson et al. |
| 9,570,273 B2 | 2/2017 | Watson et al. |
| 9,601,317 B2 | 3/2017 | Konesky |
| 10,765,850 B2 | 9/2020 | Kalghatgi et al. |
| 2011/0022043 A1 | 1/2011 | Wandke et al. |
| 2011/0171188 A1 | 7/2011 | Morfill et al. |
| 2012/0046597 A1 | 2/2012 | Morfill et al. |
| 2012/0046602 A1 | 2/2012 | Morfill et al. |
| 2012/0064016 A1 | 3/2012 | Lloyd et al. |
| 2012/0080412 A1 | 4/2012 | Holbeche et al. |
| 2012/0107761 A1 | 5/2012 | Holbeche et al. |
| 2012/0107896 A1 | 5/2012 | Wandke et al. |
| 2012/0288934 A1 | 11/2012 | Weltmann et al. |
| 2013/0026137 A1 | 1/2013 | Kindel et al. |
| 2013/0147340 A1 | 6/2013 | Holbeche |
| 2013/0345620 A1 | 12/2013 | Zemel et al. |
| 2014/0188037 A1 | 7/2014 | Jacofsky et al. |
| 2014/0188071 A1 | 7/2014 | Jacofsky et al. |
| 2014/0188097 A1 | 7/2014 | Watson et al. |
| 2014/0188195 A1 | 7/2014 | Jacofsky et al. |
| 2014/0200506 A1 | 7/2014 | Zemel et al. |
| 2014/0207053 A1 | 7/2014 | Morfill et al. |
| 2014/0341786 A1 | 11/2014 | Konesky |
| 2015/0004248 A1 | 1/2015 | Morfill et al. |
| 2015/0088234 A1 | 3/2015 | Weltmann et al. |
| 2015/0094647 A1 | 4/2015 | Kalghatgi et al. |
| 2015/0112300 A1 | 4/2015 | Glowacki et al. |
| 2015/0123711 A1 | 5/2015 | Mandela et al. |
| 2015/0151135 A1 | 6/2015 | Kalghatgi et al. |
| 2015/0157870 A1 | 6/2015 | Kalghatgi et al. |
| 2015/0209595 A1 * | 7/2015 | Kalghatgi .............. A61N 1/327 604/20 |
| 2015/0340207 A1 | 11/2015 | Holbeche |
| 2015/0343231 A1 | 12/2015 | Sanders et al. |
| 2016/0045246 A1 | 2/2016 | Stieber et al. |
| 2016/0089545 A1 | 3/2016 | Juluri et al. |
| 2016/0106993 A1 | 4/2016 | Watson et al. |
| 2016/0113701 A1 | 4/2016 | Zemel et al. |
| 2016/0166818 A1 | 6/2016 | Kalghatgi et al. |
| 2016/0220670 A1 | 8/2016 | Kalghatgi et al. |
| 2016/0236002 A1 | 8/2016 | Dirk et al. |
| 2016/0242269 A1 | 8/2016 | Dirk et al. |
| 2016/0271411 A1 | 9/2016 | Hummel et al. |
| 2016/0271412 A1 | 9/2016 | Hummel et al. |
| 2016/0331436 A1 | 11/2016 | Holbeche |
| 2016/0331437 A1 | 11/2016 | Holbeche et al. |
| 2016/0331989 A1 | 11/2016 | Cho et al. |
| 2016/0338184 A1 | 11/2016 | Holbeche |
| 2016/0338755 A1 | 11/2016 | Holbeche et al. |
| 2016/0354614 A1 | 12/2016 | Watson et al. |
| 2016/0361558 A1 | 12/2016 | Jacofsky et al. |

FOREIGN PATENT DOCUMENTS

| | | |
|---|---|---|
| EP | 3051926 A1 | 8/2016 |
| KR | 20150142162 A | 12/2015 |
| WO | 0150963 A1 | 7/2001 |
| WO | 2010107744 A1 | 9/2010 |
| WO | 2010107746 A1 | 9/2010 |
| WO | 2011058301 A1 | 5/2011 |
| WO | 2011128620 A1 | 10/2011 |
| WO | 2012106735 A2 | 8/2012 |
| WO | 2013040542 A1 | 3/2013 |
| WO | 2015071099 A1 | 5/2015 |
| WO | 2016006832 A1 | 1/2016 |
| WO | 2016020407 A1 | 2/2016 |
| WO | 2016037599 A1 | 3/2016 |
| WO | 2016128873 A1 | 8/2016 |
| WO | 2016192986 A1 | 12/2016 |
| WO | 2016192997 A1 | 12/2016 |
| WO | 2017008781 A1 | 1/2017 |

OTHER PUBLICATIONS

Search Report for International Application No. PCT/US2017/03278 dated Jul. 25, 2017.

International Search Report and Written Opinion for International Application No. PCT/US2017/019259 dated May 31, 2017.

\* cited by examiner

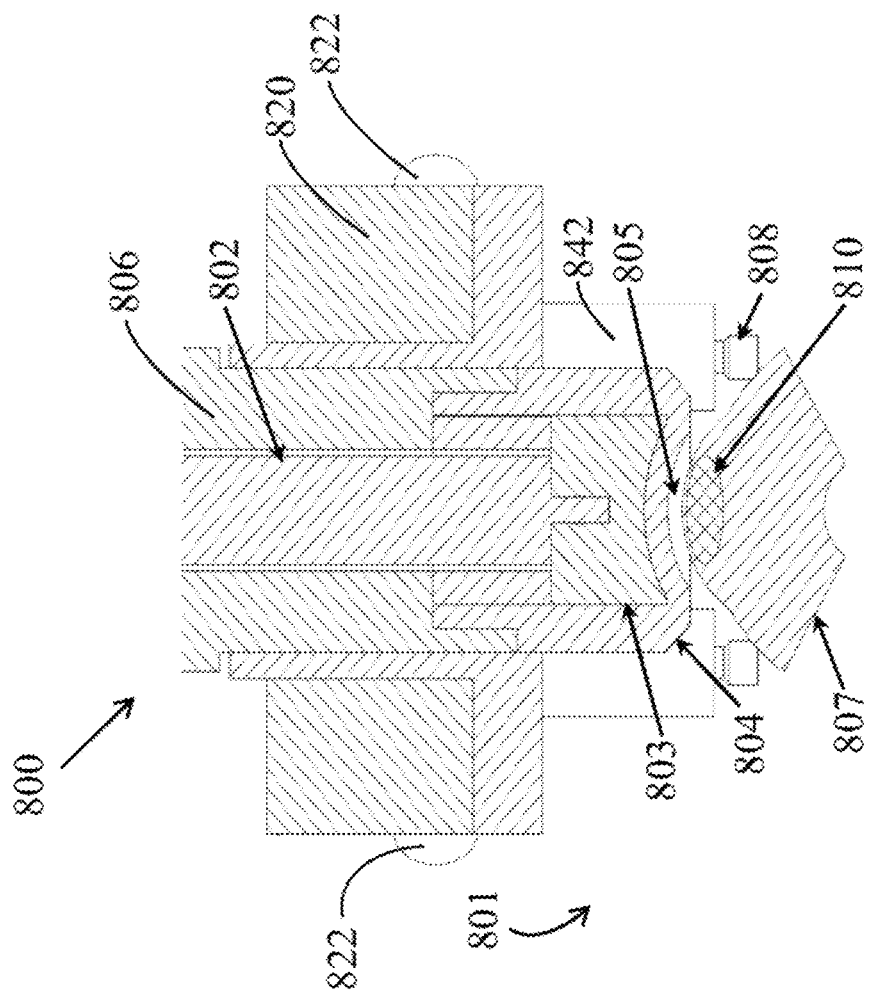
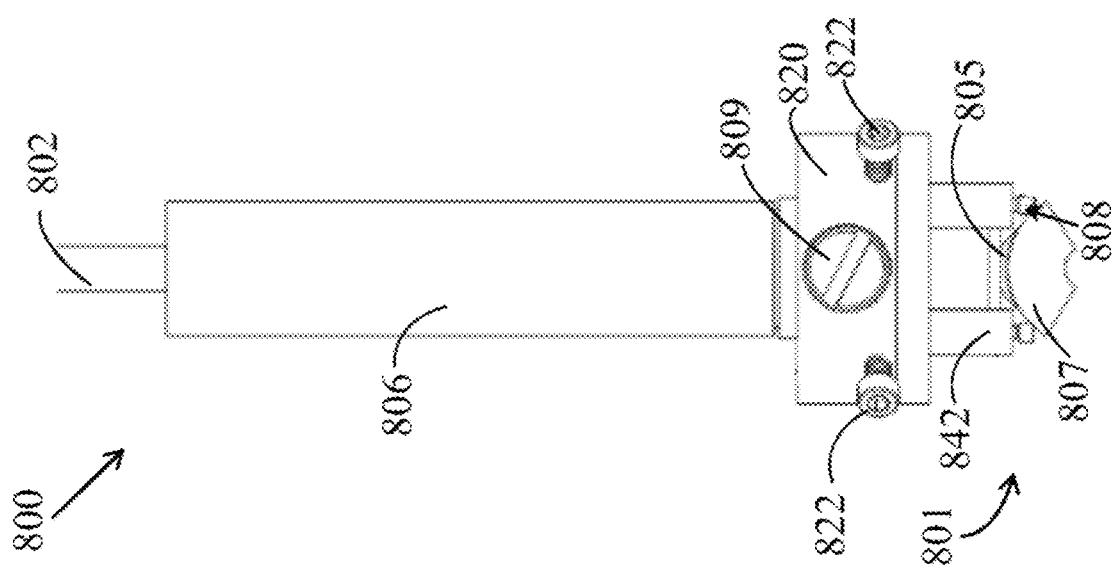

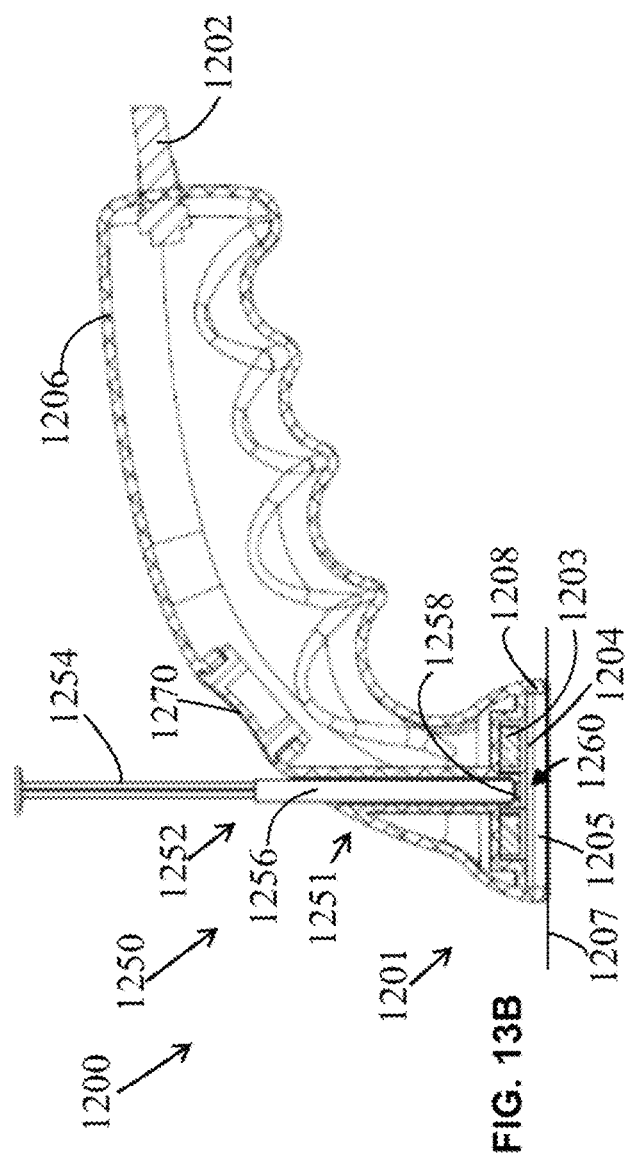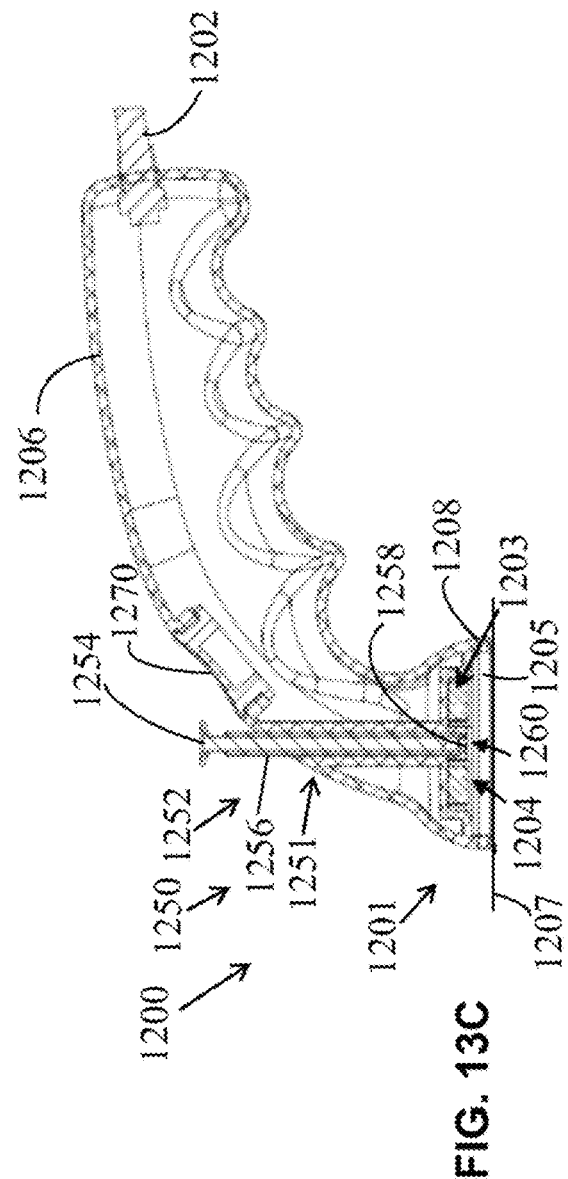

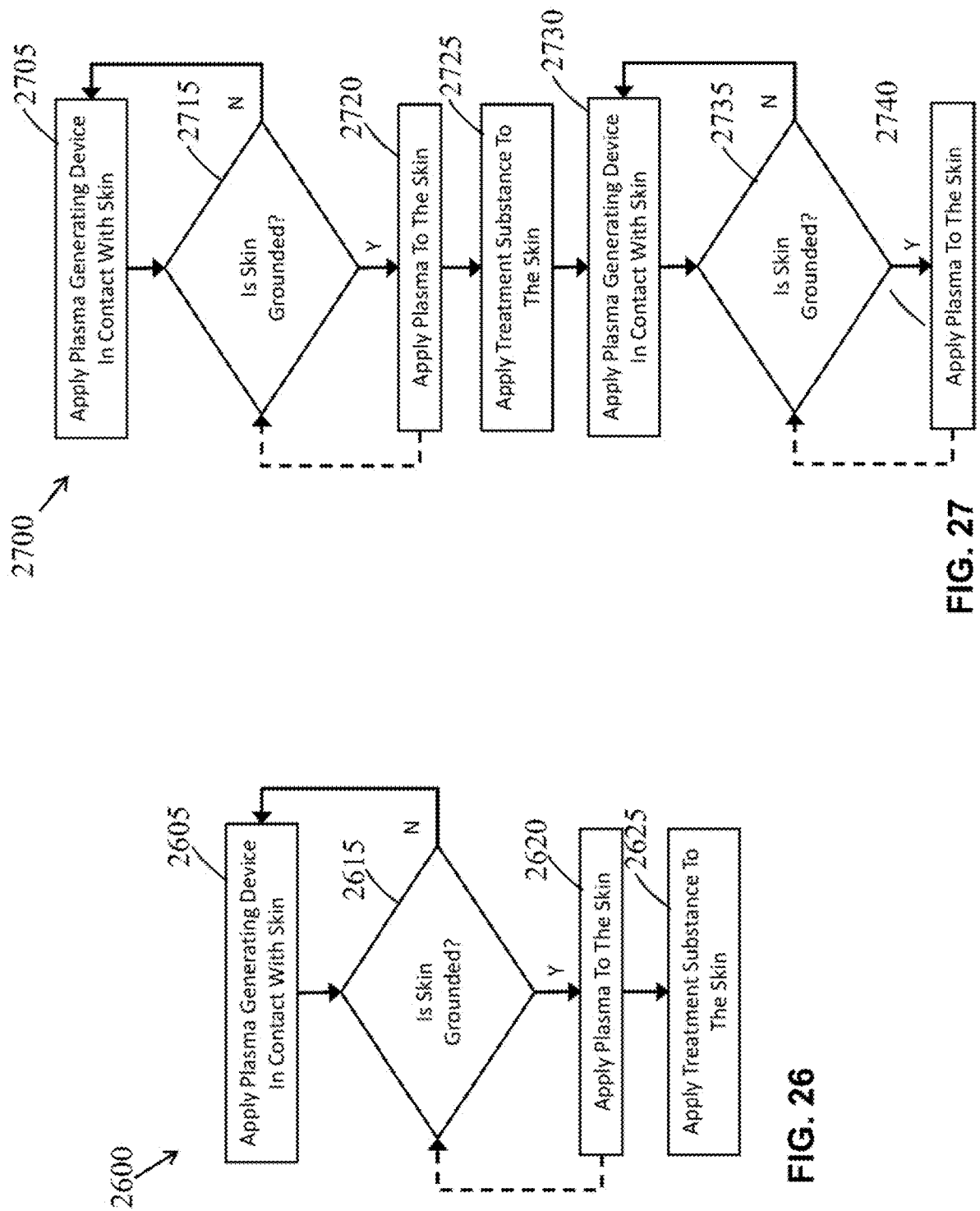

METHODS AND SYSTEMS FOR TRANS-TISSUE SUBSTANCE DELIVERY USING PLASMAPORATION

RELATED APPLICATIONS

This application is a divisional of U.S. application Ser. No. 15/592,568, filed on May 11, 2017, which claims the benefits of and priority to U.S. Provisional Application Ser. No. 62/335,323, titled METHODS AND SYSTEMS FOR TRANS-TISSUE SUBSTANCE DELIVERY USING PLASMAPORATION, which was filed on May 12, 2016, and is incorporated herein by reference in its entirety.

TECHNICAL FIELD

The present invention relates generally to methods and systems for enabling or enhancing trans-tissue substance delivery using non-thermal plasma, and more particularly for controlling the process of opening pores in skin or tissue uniformly, safely, and effectively, including, for example, for transporting one or more substances across layers of skin or tissue, including, for example, for delivery of vaccines, bioactive substances, drugs and cosmetics, deep tissue sanitization, improvement of skin health, and the like.

BACKGROUND OF THE INVENTION

Transdermal delivery of a treatment substance is localized, non-invasive, and has the potential for sustained and controlled release of various substances, including, for example, drugs and other molecules. In addition, transdermal delivery avoids first-pass metabolism, which reduces the concentration of certain substances before the substance reaches the circulatory system. In addition, percutaneous absorption can minimize the risk of irritation of the gastrointestinal tract and minimize pain and other complications associated with parenteral administration.

Transdermal delivery, however, requires molecules to pass through the skin. The outer layer of the skin is the stratum corneum ("SC"). The SC is composed of dead, flattened, keratin-rich cells, called corneocytes. These dense cells are surrounded by a complex mixture of intercellular lipids—namely, ceramides, free fatty acids, cholesterol and cholesterol sulfate. The predominant diffusional path for a molecule crossing the SC appears to be intercellular. The remaining layers of the skin are the epidermis (viable epidermis), the dermis, and the subcutaneous tissue.

Only a small percentage of substances or compounds can be delivered transdermally because skin has barrier properties, namely the highly lipophilic SC, that prevents molecules from penetrating the skin. As a result, only, molecules with a molecular weight (MW) of less than 500 Dalton can be administered topically or percutaneously. Often, for pharmaceutical applications, the development of innovative compounds is restricted to a MW of less than 500 Dalton when topical dermatological therapy, percutaneous systemic therapy or vaccination is the objective. In addition, transport of most drugs across the skin is very slow, and lag times to reach steady-state fluxes are measured in hours. Achievement of a therapeutically effective drug level is therefore difficult without artificially enhancing skin permeation.

A number of chemical and physical enhancement techniques have been developed in an attempt to compromise the skin barrier function in a reversible manner. These attempts may be classified as passive and active methods.

Passive methods for enhancing transdermal drug delivery include the use of vehicles such as ointments, creams, gels and passive patch technology. In addition, there are other passive methods that artificially damage the barrier in order to allow improved permeation of active substances, such as, for example, micro-needles that produce small physical holes having a depth of approximately 100-200 μm in the skin to allow improved permeation. The amount of substance that can be delivered using these methods is limited because the barrier properties of the skin are not fundamentally changed.

Current or other mode of delivery techniques may include injection using a needle, administering drugs through the skin via electroporation, and administering drugs using microneedles. Needles have the disadvantage of being painful and are invasive to the skin. Electroporation is both painful and invasive. Other attempts to enhance transdermal drug delivery, including using sonoporation, iontophoresis, etc., have inherent limitations as well, including, for example, long lag times to reach therapeutic levels or are limited by the physicochemical properties of the drug being delivered. Active methods for enhancing transdermal drug delivery systems involve the use of external energy to act as a driving force and/or act to reduce the SC barrier resistance and enhance permeation of drug molecules into the skin. Iontophoresis and electroporation are two common methods of active transdermal drug delivery systems.

Iontophoresis is the process of increasing the permeation of charged or polar drugs into skin by the application of an electric current. The amount of a compound delivered is directly proportional to the quantity of charge passed; i.e., it depends on the applied current, the duration of current application and the surface area of the skin in contact with the active electrode compartment. Advantages of iontophoresis include an improved onset time and also a more rapid offset time—that is, once the current is switched off, there is no further transportation of the compound.

To deliver drugs using iontophoresis, a drug is applied under an electrode of the same charge as the drug and return electrode having an opposite charge is placed on the body surface. A current below the level of the patient's pain threshold is applied for an appropriate length of time. Because like charges repel one another, the electrical current increases the permeation of the drug into surface tissues, without altering the structure of the SC. Iontophoresis transports drugs primarily through existing pathways in skin, such as hair follicles and sweat glands. Iontophoresis is typically used when a low level delivery is desired over a long time period. Iontophoresis involves the use of relatively low transdermal voltages (<100 V). Iontophoresis cannot be used to deliver molecules or drugs that do not carry a charge.

Transdermal absorption of drugs through iontophoresis is affected by drug concentration, polarity of drugs, pH of donor solution, ionic competition, ionic strength, electrode polarity, etc. Iontophoresis has safety concerns due to the use of electrical contacts on the skin, which may result in patient discomfort, pain and, sometimes, even skin damage and burns.

Electroporation is a method for transdermal drug delivery that consists of applying high-voltage pulses to skin. The applied high-voltage plays a dual role. First, it creates new pathways for enhancing drug permeability and second, it provides an electrical force for driving like charged molecules through the newly created pores. Electroporation is usually used on the unilamellar phospholipid bilayers of cell membranes. However, it has been demonstrated that electroporation of skin is feasible, even though the SC contains multilamellar, intercellular lipid bilayers with phospholipids and no living cells.

Electroporation of skin requires high transdermal voltages (~100 V or more, usually >100 V). In transdermal electroporation, the predominant voltage drop of an applied electric pulse to the skin develops across the SC. This voltage distribution causes electric breakdown (electroporation) of the SC. If the voltage of the applied pulses exceeds a voltage threshold of about 75 to 100 V, micro channels or "local transport regions" are created through the breakdown sites of the SC.

DNA introduction is the most common use for electroporation. Electroporation of isolated cells has also been used for (1) introduction of enzymes, antibodies, and other biochemical reagents for intracellular assays; (2) selective biochemical loading of one size cell in the presence of many smaller cells; (3) introduction of virus and other particles; (4) cell killing under nontoxic conditions; and (5) insertion of membrane macromolecules into the cell membrane.

The presence of electrodes in contact with skin/tissue (or inserted into skin/tissue) and the delivery of current into skin/tissue in this manner leads to patient discomfort, muscle contractions, moderate to severe pain and, sometimes, even skin damage and burns. In addition, electroporation often takes hours, e.g., 6 to 24 hours, to drive therapeutic amount of drugs or other molecules transdermally.

U.S. Pat. No. 8,455,228, entitled "Method to Facilitate Directed Delivery and Electroporation Using a Charged Steam," state that "the method and apparatus in accordance with the present invention are effective in using an electrical field to adjust the electrochemical potential of a target molecule thereby providing molecular transport of the target molecule into and/or across the tissue by a diffusive transport mechanism." The '228 patent discloses a first embodiment with dielectric properties to assure that it will hold a charge sufficient to polarize charged entities contained within a vessel and a plurality of electroporation applicators. The process described in the '228 patent disclosure suffers from several deficiencies. First, it requires molecules that may be polarized or charged, second it requires electroporation applicators, and third, the molecule is contacted with plasma during the process, which may irreversibly modify the molecular structure leading to adverse results. In addition it is well known that interaction of molecules with plasma leads to the oxidation of such molecules, which may irreversibly alter the structure and function of the molecules.

The '228 patent also discloses a second embodiment utilizing a plasma jet with a ground ring around an inner chamber. The disclosure related to this device includes containing cells suspended in fluid in the inner chamber and promoting uptake into the cells; or injecting plasmid intradermally and exposing the injection site to plasma.

US patent publication No. 2014/0188071 discloses a method of applying a substance to the skin and applying plasma to the same area. The '071 publication discloses an open cell foam to hold a drug, water, etc., and applies plasma through the open cell foam. Applying plasma through the open cell foam and contacting the drugs with plasma may irreversibly alter the molecular structure and/or function of the drugs and cause undesirable side effects and/or render the drug ineffective.

US patent publication 2012/0288934 discloses a plasma jet and the active substance is applied to the skin with the gas stream of the plasma jet and is transported onto the region of the living cells through the barrier door that has been opened by the plasma. Applying the active substance with the gas stream of the plasma jet may irreversibly alter the molecular structure and/or function of the active substance and cause undesirable side effects and/or render the active substance ineffective.

SUMMARY

According to one aspect of the present invention, a method of treating skin includes applying a treatment patch to the skin, wherein the treatment patch includes a treatment substance, applying a plasma to the skin, and exposing the treatment substance to the skin.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention.

FIG. 8A is a drawing of an exemplary skin treatment apparatus for trans-tissue substance delivery on contoured skin surfaces.

FIG. 8B is a cross-section drawing of the lower portion of the exemplary skin treatment apparatus shown in FIG. 8A.

FIG. 13B is a cross-section drawing of the exemplary skin treatment apparatus shown in FIG. 12 with a syringe placed into the cavity.

FIG. 13C is a cross-section drawing of the exemplary skin treatment apparatus shown in FIG. 12 with a plunger actuated.

FIG. 26 is a flow diagram of another exemplary method of treating grounded skin with plasma.

FIG. 27 is a flow diagram of another exemplary method of treating grounded skin with plasma.

DESCRIPTION

Figure 1B:
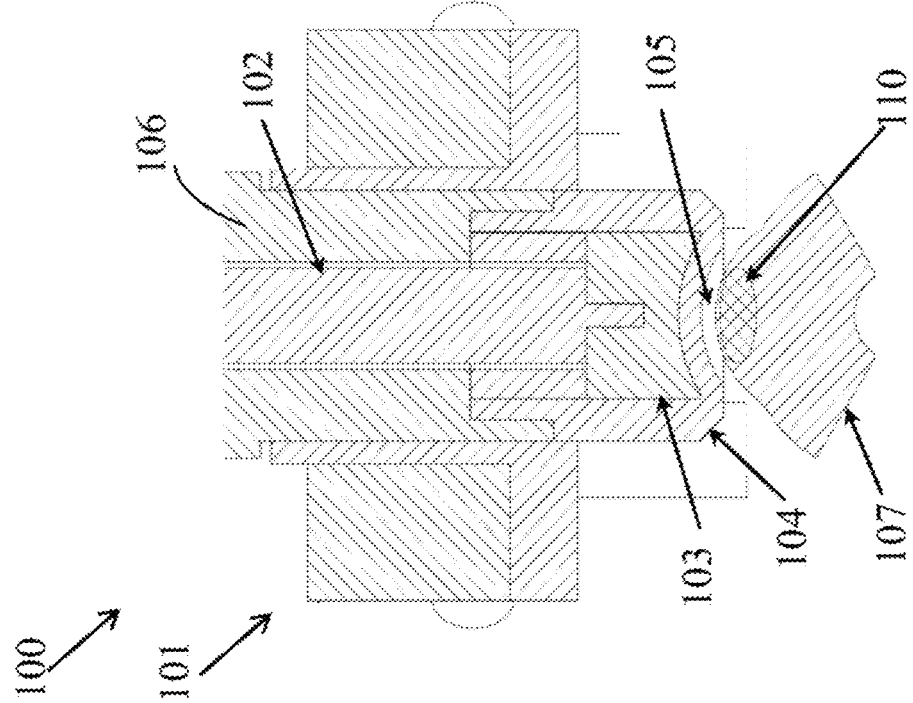
FIG. 1B illustrates a cross section of the plasma generation portion of the exemplary apparatus shown in FIG. 1A.

The following includes definitions of exemplary terms used throughout the disclosure. Both singular and plural forms of all terms fall within each meaning:

"Bioactive substance," as used herein includes, but is not limited to, antifungals, antimicrobials, opioids, growth factors, polynucleotides, oligonucleotides, peptides, RNAs, DNA plasmids, DNA-vaccines, RNA based vaccines, protein based vaccines, nanoparticles, liposomes, micelles, vesicles, quantum dots, cytokines, chemokines, antibodies, drugs such as, for example, non-steroidal anti-inflammatory drugs (NSAID's), biologics, such as, for example monoclonal antibodies or other proteins and peptides, and the like that may be delivered intercellularly, intracellularly, or both intercellularly and intracellularly via the plasmaporation devices disclosed herein.

"Circuit" or "circuitry," as used herein includes, but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software. As used herein, "circuit" is considered synonymous with "logic."

"Controller," as used herein includes, but is not limited to, any circuit or device that coordinates and controls the operation of one or more input or output devices. For example, a controller can include a device having one or more processors, microprocessors, or central processing units (CPUs) capable of being programmed to perform input or output functions.

"Logic," as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software. As used herein, "logic" is considered synonymous with "circuit."

"Operative communication" or "circuit communication," as used herein includes, but is not limited to, a communicative relationship between devices, logic, or circuits, including mechanical and pneumatic relationships. Direct electrical, electromagnetic, and optical connections and indirect electrical, electromagnetic, and optical connections are examples of such communications. Linkages, gears, chains, push rods, cams, keys, attaching hardware, and other components facilitating mechanical connections are also examples of such communications. Pneumatic devices and interconnecting pneumatic tubing may also contribute to operative communications. Two devices are in operative communication if an action from one causes an effect in the other, regardless of whether the action is modified by some other device. For example, two devices separated by one or more of the following: i) amplifiers, ii) filters, iii) transformers, iv) optical isolators, v) digital or analog buffers, vi) analog integrators, vii) other electronic circuitry, viii) fiber optic transceivers, ix) Bluetooth communications links, x) 802.11 communications links, xi) satellite communication links, xii) near-field communication, and xiii) other wireless communication links. As another example, an electromagnetic sensor is in operative communication with a signal if it receives electromagnetic radiation from the signal. As a final example, two devices not directly connected to each other, but both capable of interfacing with a third device, e.g., a central processing unit (CPU), are in operative communication.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system, or other types of executable instructions. It will be appreciated by one of ordinary skill in the art that the form of software is dependent on, for example, requirements of a desired application, the environment it runs on, or the desires of a designer/programmer or the like.

While the above exemplary definitions have been provided, it is Applicant's intention that the broadest reasonable interpretation consistent with this specification be used for these and other terms.

Applicants have developed techniques for trans-tissue substance delivery treatments that can include moving substances, molecules, drugs, DNA and the like into and/or through tissue, for example, across layers of the skin, both intercellularly (between cells) and intracellularly (into the cells) using plasma. The descriptions herein may refer to skin as an exemplary tissue and skin treatment as an exemplary tissue treatment. However, these descriptions are additionally applicable to tissue and tissue treatment generally. Applicants filed U.S. Provisional Application Ser. No. 61/883,701 filed on Sep. 27, 2013 and U.S. Non-Provisional application Ser. No. 14/500,144, filed on Sep. 29, 2014, both of which are entitled Method and Apparatus for Delivery of Molecules Across Layers of the Skin, and both are incorporated herein by reference in their entirety. Applicants' exemplary methods utilize plasma for providing a safe, contact-less delivery and cellular uptake of various substances, which may be referred to herein as plasmaporation. Applicants also filed U.S. Provisional Application Ser. No. 61/911,536 filed on Dec. 4, 2013 and U.S. Non-Provisional application Ser. No. 14/560,343 filed on Dec. 4, 2014, both of which are entitled Transdermal Delivery of DNA Vaccines Using Non-Thermal Plasma, and are both incorporated herein by reference in their entirety. Applicants also filed U.S. Provisional Application Ser. No. 62/299,783 filed on Feb. 25, 2016 entitled Methods and Systems for Controlling or Tuning the Electric Field Generated in Skin or Tissue During Cold Plasma Skin Treatments, and is incorporated herein by reference in its entirety.

Plasmaporation uses non-thermal (cold) plasma, the fourth state of matter, for enabling transdermal delivery of molecules, drugs, vaccines and the like through tissue and into cells via creation of temporary pores in the stratum corneum and or the cell membrane. Non-thermal plasma is a partially ionized gas generated at atmospheric pressure using ambient air or other gases and electricity. It is generated by the breakdown of air or other gases present between two electrodes, at least one of which is insulated, under the application of sufficiently high voltage. A pulsed electric field used to generate the plasma opens up temporary pores in the skin and within cell membranes to promote transdermal delivery and cellular uptake of molecules (including macromolecules), drugs, vaccines and the like. In some embodiments, for example, the temporary pores remain open for about 1 to about 5 minutes.

The electrode(s) generating the plasma are not in contact with the tissue (e.g., skin), no needles are required, and generation of non-thermal plasma directly on skin is rapid and painless. The plasma is generated as long as the applied voltage is on. In exemplary embodiments with configurations where the electrodes are insulated, non-thermal plasma is formed by dielectric barrier discharge (DBD), which is safe and painless when applied to skin. The dielectric barrier is an important part of a DBD generating device and its function is to prevent the flow of conduction current from high voltage electrode to the substrate being treated. The devices and techniques described herein result in more efficient and rapid means of achieving plasmaporation for trans-tissue substance delivery in a painless manner without the need for injection. Accordingly, the plasmaporation devices and techniques described herein can promote efficient intercellular delivery and intracellular uptake of various substances, including, for example, molecules, drugs, vaccines, and the like.

The plasmaporation device and methods of the present disclosure provide efficient intercellular, intracellular, or both intercellular and intracellular delivery and uptake of substances, including for example, bioactive substances by creating temporary pores in the target area (cells or tissue) of a subject using plasma. A bioactive substance as discussed herein refers to a fluid, i.e., gas or liquid, comprising molecules, drugs, vaccines, biologics, such as monoclonal antibodies or other proteins and peptides, and the like that may be delivered intercellularly, intracellularly, or both intercellularly and intracellularly to the subject. Non-limiting examples of such bioactive substances include antifungals, antimicrobials, opioids, growth factors, polynucleotides, oligonucleotides, peptides, RNAs, DNA plasmids, DNA based vaccines, RNA based vaccines, protein based vaccines, nanoparticles, micelles, vesicles, quantum dots, cytokines, chemokines, antibodies, liposomes, and drugs including, but not limited to, nonsteroidal anti-inflammatory drugs (NSAID's).

Exemplary bioactive substances, cosmetics and other substances that may be used with the present invention are disclosed in U.S. Pat. Pub. No. 2015/0094647 titled METHODS AND APPARATUS FOR DELIVERY OF MOLECULES ACROSS LAYERS OF TISSUE filed on Sep. 29, 2014, which is incorporated herein in its entirety for its disclosure on exemplary bioactive substances, cosmetics and other substances that may be used with the present invention.

The plasmaporation device and methods of the present disclosure also provide efficient intercellular, intracellular, or both intercellular and intracellular delivery and uptake of fluids, i.e., gases or liquids, comprising cosmetic substances by creating temporary pores in the target area (cells or tissue) of a subject using plasma. Non-limiting examples of such cosmetic substances include botulinum toxin A or B (Botox), hyaluronic acid, collagen, moisturizers, growth factors, antiwrinkle creams, emollients, ointments, and the like. In some embodiments, cosmetice include chemical enhancers, such as, dimethyl sulfoxide, azone, pyrrolidones, oxazolidinones, urea, oleic acid, ethanol, liposomes and the like.

Embodiments that disclose use of the present invention with various substances, including, for example, bioactive substances or cosmetics, are meant to include other substances and are not limited to these identified categories and may include other substances, such as, for example, those disclosed herein or incorporated herein.

Plasmaporation has a number of other practical applications. In some embodiments, plasmaporation may be used to increase permeation of sanitizers, antimicrobials, surgical scrubs, and the like. Plasmaporation may be also be used to treat acne. First, plasmaporation may open the existing clogged pores as well as surrounding pores and sterilize the infected area. Second, plasmaporation allows antimicrobials and other acne medication to enter the pores. Plasmaporation may be also used to open pores and drive cosmetic related materials, such as, for example, collagen, BOTOX or other fillers into the skin to reduce wrinkles. Plasmaporation may be used to increase the absorption rate of moisturizers and thereby minimizes the "tack" associated with moisturizers that have not been fully absorbed.

In some embodiments, skin may be preconditioned to temporarily alter the skin pH, moisture level, temperature, electrolyte concentration or the like. Preconditioning helps maximize speed and depth of permeation of active ingredients through pore formation without harming the skin.

In some embodiments, plasmaporation may be used in combination with low levels of non-irritating chemical skin permeation enhancers to achieve synergistic permeation of actives, including antimicrobials, cosmetic ingredients, vaccines, or drugs. Examples of chemical enhancers include dimethyl sulfoxide, azone, pyrrolidones, oxazolidinones, urea, oleic acid, ethanol, liposomes.

In some exemplary embodiments, plasmaporation involves the use of a planar DBD or a DBD jet plasma generator for needle-free transdermal delivery of macromolecules. Depending on the plasma dose, the depth of penetration of the macromolecules can be controlled to ensure delivery to a certain region of the skin, for example, a target layer such as the stratum corneum, viable epidermis, and/or dermis.

Applicants have demonstrated that plasmaporation can enhance transdermal delivery of topically applied dextran molecules with molecular weights up to 70 kDa across ex vivo porcine skin within 15 minutes and without creating skin damage, as described in the patent applications entitled Method and Apparatus for Delivery of Molecules Across Layers of the Skin on Sep. 27, 2013 and Sep. 29, 2013 incorporated herein. Others devices and techniques are described in U.S. Non-Provisional application Ser. No. 14/564,717 filed on Dec. 9, 2014, U.S. Non-Provisional application Ser. No. 14/610,467 filed on Jan. 30, 2015, and U.S. Non-Provisional application Ser. No. 14/967,512 filed on Dec. 14, 2015. All of these applications are incorporated by reference herein in their entirety.

The exemplary embodiments of apparatuses and methods disclosed herein use non-thermal plasmas to enable delivery of macromolecules, drugs, vaccines and the like, through the surface and into skin without harming the skin. Non-thermal plasma enabled skin poration provides a non-invasive, safe means for delivery and intracellular uptake of molecules, drugs and vaccines at room temperature and atmospheric pressure without the possible pain and other adverse side effects associated with electroporation. An additional benefit of using non-thermal plasma is that the generated reactive species sterilizes the skin during plasmaporation.

In the plasma phase, neutral gas atoms (or molecules), electrons, positive/negative ions, and radicals are generated. Their generation and concentration depend, in part, on the physical and chemical properties of the gas being used to generate the plasma as well as the electrical parameters used to generate the plasma. The strength of the electric field generated by non-thermal plasma on skin can be tuned in various ways, including, for example, by varying the time of plasma treatment; by varying the gap between the electrode and the skin; by varying the applied voltage; by varying the pulse duration; by varying the frequency; by varying the duty cycle; by adding conductive elements in contact with the skin; by varying the configurations and shapes of the conductive elements; by varying the placement of the conductive elements; by adding circuitry in operative communication with the conductive elements; by adjusting variable features or components of the circuitry; etc. These parameters can allow for the control of the depth and delivery amount of various substances associated with trans-tissue substance delivery, including, for example, macromolecules, drugs, vaccines and the like. Tuning and controlling the depth and distribution of the electric field generated during plasma-treatment of skin can allow the trans-tissue substance delivery to be directed to a targeted region of tissue, for example, a particular skin layer or layers, with an optimal dose and/or delivery process.

Maintaining a consistent gap between the high-voltage electrode that creates the plasma (and its associated dielectric in a DBD system) and the tissue provides for an evenly distributed treatment to the tissue, including, for example, skin, eye, and/or mucosa. When high voltage is applied to the electrode from the power supply, cold plasma is generated in the air gap between the skin and the dielectric. The electric field created by the plasma porates the skin so that substances may be delivered through the skin. In some embodiments, as discussed below, spacers may be used to place the high-voltage electrode of the plasma generating device a predefined distance over the skin. However, in embodiments where the surface of the skin to be treated is not substantially flat, a flat electrode, even when used with spacers, cannot be located in a manner that provides a consistent air gap between the electrode and a contoured skin surface.

The high voltage electrode and dielectric can be shaped or contoured to conform to the skin surface shape or contour. A contoured dielectric/electrode can be shaped in such a manner as to mimic the contour of the skin being treated. For example, in one embodiment, an electrode can be contoured to match the contour of a finger, i.e., with a similar radius. A contoured electrode/dielectric can provide a constant air gap between the dielectric outer surface and the skin, resulting in a consistent gap for the plasma. If a flat electrode is used on a contoured surface, the plasma is non-uniform and plasma may not even be generated in areas where it is needed because the gap may be too large. If the plasma air gap is non-uniform, plasma will likely be formed locally in the smallest part of the air gap. The plasma may also be too intense in the small gap area such that it may cause localized burning of the skin.

Grounding can also improve the consistency and safety of the electric field. In some embodiments, the skin to be treated can be grounded. Grounding can reduce the risk of shock and pain by making the plasma more uniform and homogeneous. In one embodiment, the ground can be attached to the skin near the plasma treatment area using a conductor attached to the ground of the power supply. For example, this could be done by connecting a grounded wire to conductive tape in contact with the skin in the area of treatment. In other embodiments, as discussed in more detail below, the ground can be integrated into the plasma generating device so that when the device is applied to the skin, the skin becomes locally grounded by being in contact with the grounded conductor integrated into the device. In some embodiments, also discussed below, the grounded conductor can be spring loaded so that solid contact between the ground and skin is ensured by the spring pressure on the grounded conductor. Furthermore, a conductive element, acting as a second electrode can be used. In this embodiment, the first electrode is high voltage and second electrode can be grounded or at a bias voltage, including, for example, a high voltage with opposite polarity to that of the first electrode.

In yet other embodiments, substance delivery systems can be used with the plasma generating device to improve the delivery of the treatment substance to the treated skin. Such substance delivery systems, as discussed in detail below, can be manual or automatic. In some embodiments, the same device can be integrated with various components to both porate the skin and deliver a treatment substance to the skin.

Figure 1A:
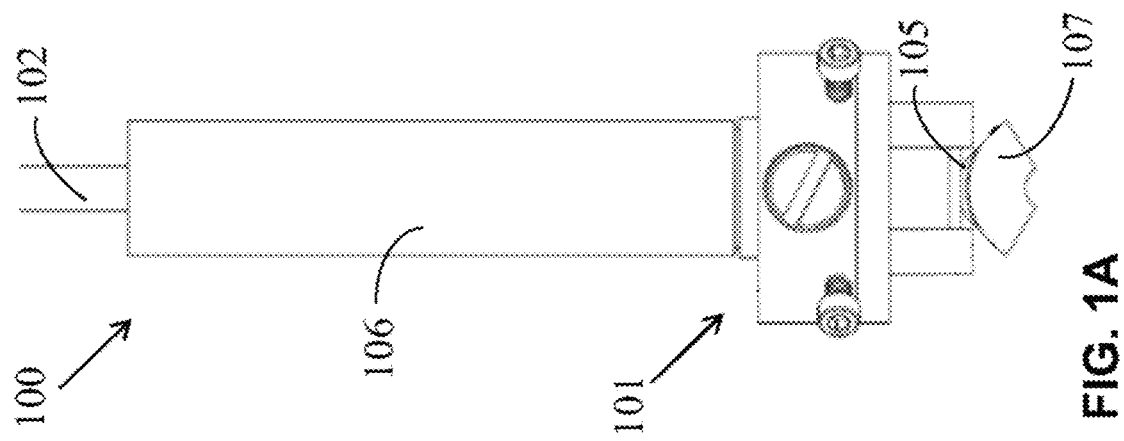
FIG. 1A illustrates an exemplary skin treatment apparatus for trans-tissue substance delivery on contoured skin surfaces.

FIG. 1A illustrates an exemplary skin treatment apparatus that includes an exemplary skin treatment system 100 for trans-tissue substance delivery on contoured skin surfaces. FIG. 1B illustrates a cross section of the plasma generation portion of the exemplary skin treatment system 100. Skin treatment system 100 includes a plasma generator 101. Plasma generator 101 includes a high voltage cable 102 connected to an electrode 103 on a first end and a high voltage power supply (not shown) on the second end. The power supply can be a pulsed DC, AC, pulsed AC, RF, microwave, or any other suitable power supply. The power supply may utilize one or more different wave forms, such as, for example, a constant, ramp-up, ramp-down, pulsed, nanosecond pulsed, microsecond pulsed, square, sinusoidal, random, in-phase, out-of-phase, and the like. In exemplary embodiments, the power supply generates microsecond (1-10 µs) and nanosecond (1-500 ns) duration pulses. In exemplary embodiments, the applied voltage can range from about 3 kV to about 30 kV with an operating frequency range from about 10 Hz to about 30 kHz. In exemplary embodiments, the power supply can operate in a continuous mode (e.g., for about 1-120 seconds) or in a pulsed mode (e.g., for about 1-100,000 pulses). In one embodiment, the pulses can be triggered manually, for example, for about 1 to about 200 pulses. In another embodiment, the pulses can be triggered automatically, for example, for about 1 to about 100,000 pulses. In any of these embodiments, the pulse duration and pulse interval may be separately specified or controlled. In various embodiments, the skin treatment time can range from a single pulse (e.g., about 10 ns) to a few minutes (e.g., about 120 s). In other embodiments, the pulses comprise a duty cycle from about 1% to about 100%. In other embodiments, the power supply can be battery-driven, integrated into the plasma generator 101 with the electrode 103, and/or part of an application, detection, and quantification module.

In this exemplary embodiment, plasma generator 101 is a non-thermal dielectric barrier discharge (DBD) generator. A dielectric barrier 104, for example, a quartz, Teflon, alumina, or dielectric of another material, is located below the high voltage electrode 103. Plasma can be generated across gap 105 using this type of plasma generator, for example, by applying an alternating polarity pulsed voltage with nanosecond duration pulses. In one embodiment, the applied voltage may have a pulse width of between about 40-500 ns (single pulse to 20 kHz) with a rise time of 0.5-1 kV/ns and a magnitude of about 20 kV (peak-to-peak) at a power density of 0.01-100 W/cm$^2$. In one embodiment, Teflon can be used as the insulating dielectric barrier 104 that covers the electrode 103. In other embodiments, other dielectric barriers may be used, including, for example, quartz, An exemplary electrode 103 includes about a 11.1 mm diameter aluminum electrode. In other embodiments, other electrode materials may be used, including, for example, copper, Any size dielectric and electrode suitable for a particular application may be used. The high voltage electrode 103 and dielectric barrier 104 can be located within a housing 106, along with additional components.

In this embodiment, the electrode 103 and dielectric barrier 104 are contoured with a radius that aligns with the contour of the skin 107 in the skin treatment area. In various other embodiments, the contour of the electrode 103 and dielectric 104 can be shaped to mimic the shape of any skin to be treated. This contouring will form a uniform air gap 105 between the skin 107 and the dielectric 104 in which uniform plasma can be created. This uniform plasma can evenly affect the target treatment area of the skin 107, shown with an exemplary treatment substance 110. In this configuration, the uniform gap 105 can result in a uniform plasma in the target treatment area of the skin 107 before and/or after the treatment substance 110 is delivered to the target treatment area of the skin 107.

The electrode 103 can be contoured to match the shape of the contoured dielectric 104. If any air gaps are created between the dielectric 104 and the high voltage electrode 103 within the generator 101, for example, due to manufacturing tolerances, the air gaps can be eliminated by the use of dielectric grease or other conformable dielectric material. In one embodiment, the discharge gap 105 between the dielectric barrier 104 and the skin 107 is consistently about 3 mm±1 mm throughout the contoured treatment area.

In various embodiments, the skin 107, dielectric, 104, and/or electrode 103 may have various shapes, including, for example, curved shapes (including, e.g., convex and/or concave), combinations of curved and flat portions, etc. In all of these embodiments, the gap between the outer dielectric surface and the skin surface is substantially consistent throughout the skin treatment area.

The electric field associated with the plasma is directed through at least a region of the skin 107, depositing electrical charges that can develop a voltage potential across the skin, which leads to intracellular and intercellular poration. Providing a consistent air gap 105 for the plasma results in a more controlled and consistent electric field in the skin 107. Even with the aforementioned contours, the plasmaporation is non-invasive since the electrode 103 is not in contact with the skin 107 being treated.

With respect to intracellular poration, the transmembrane voltage of fluid lipid bilayer membranes reaches at least about 0.2 V. The transmembrane voltage charges the lipid bilayer membranes, causes rapid, localized structural rearrangements within the membrane and causes transitions to water-filled membrane structures, which perforate the membrane forming "aqueous pathways" or "pores." The aqueous pathways or pores allow an overall increase in ionic and molecular transport. The transmembrane voltage is believed to create primary membrane "pores" with a minimum radius of about approximately 1 nm. In addition, the applied electric field results in rapid polarization changes that deform mechanically unconstrained cell membranes (e.g., suspended vesicles and cells) and cause ionic charge redistribution governed by electrolyte conductivities.

The electrical pulses used to generate the plasma also cause intercellular poration. The SC, which is about 15-25 μm thick, is the most electrically resistive part of skin. The application of electrical pulses used to generate the plasma can give rise to a transdermal voltage ranging between about 50V and about 100V, which can cause poration of the multilamellar bilayers within the SC. At these levels of applied transdermal voltage, poration of cell linings of sweat ducts and hair follicles could also occur.

Upon stoppage of the plasma or removal of the plasma generator 101 from the treated area, the pores of the skin 107 tend to close again and thus, the process is reversible. Some pores may remain open for an extended period of time, during which molecules of a treatment substance can continue to cross the cell membrane via diffusion. It has been discovered that in some embodiments, the pores of the skin 107 remain open for less than about 5 minutes. Experimental results demonstrated that a 10 kDa Dextran molecule applied to a plasma treated area was transported through open pores in the SC when applied within 0 to about 5 minutes. In this embodiment, after 5 minutes, the 10 kDa Dextran molecules no longer passed through the SC. Experimental results also demonstrated that smaller molecules like nicotine or caffeine were transported through open pores in the SC when applied within 0-20 minutes. In this embodiment, after 20 minutes, the small molecules no longer passed through the SC.

When electric pulses are applied to the skin, the absorbed energy can cause localized heating and damage to the skin. Energy greater than 50 J/cm$^2$ deposited on intact skin results in second degree burns and thermal damage to the underlying intact skin. One method of overcoming this problem is to apply short duration pulses repetitively, which allows the same or a higher amount of energy that would otherwise cause damage to be transferred without causing localized heating and skin damage. In some embodiments, the energy deposited on intact skin is less than about 25 J/cm$^2$, in some embodiments, the energy deposited on intact skin is less than about 10 J/cm$^2$, in some embodiments, the energy deposited on intact skin is less than about 5 J/cm$^2$, and in some embodiments, the energy deposited on intact skin is less than about 3 J/cm$^2$. However, when treating wounds, the energy may be increased to, for example, 500 J/cm$^2$, without causing burns.

In addition, damage to the skin may occur from localized plasma micro-discharges, also known as "streamers," that occur with non-uniform electric fields. This problem may be overcome by creating a uniform electric field, including, for example, by incorporation of the contoured electrode 103 and dielectric 104. Use of nanosecond or shorter duration pulses for the applied voltage may also be useful. Also, skin damage can be avoided by reducing the power level, frequency, duty cycle and pulse duration of the power supply and by increasing the spacing between the electrode 103 and the skin 107 to be treated.

Typically, plasma is applied directly to the skin being treated, which means the electric field is directed only in one direction, which is directly into the skin. In situations with contoured skin surfaces, it is difficult to achieve an even distribution of the electric field in the skin. By utilizing a contoured electrode, such as, for example, the contoured electrode 103 shown in FIG. 1 above, the electric field in the skin 107 can be controlled and also the strength of the electric field can be focused to be stronger in certain portions of contoured skin 107, such as, for example, typical treatment target areas of the skin: the SC and epidermis.

Figure 2B:
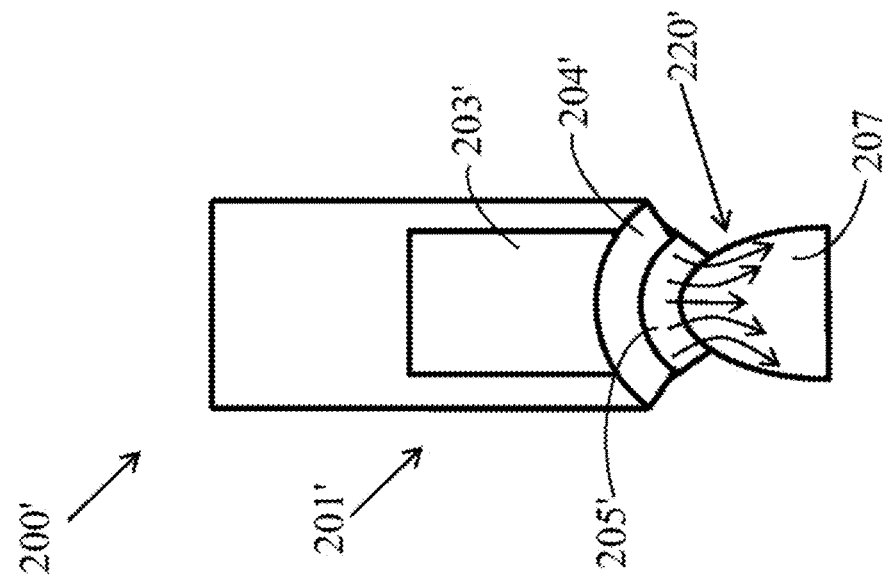
FIG. 2B illustrates a cross-section view of an exemplary skin treatment apparatus for trans-tissue substance delivery and depictions of the electric field associated with the generated plasma with a contoured electrode.
Figure 2A:
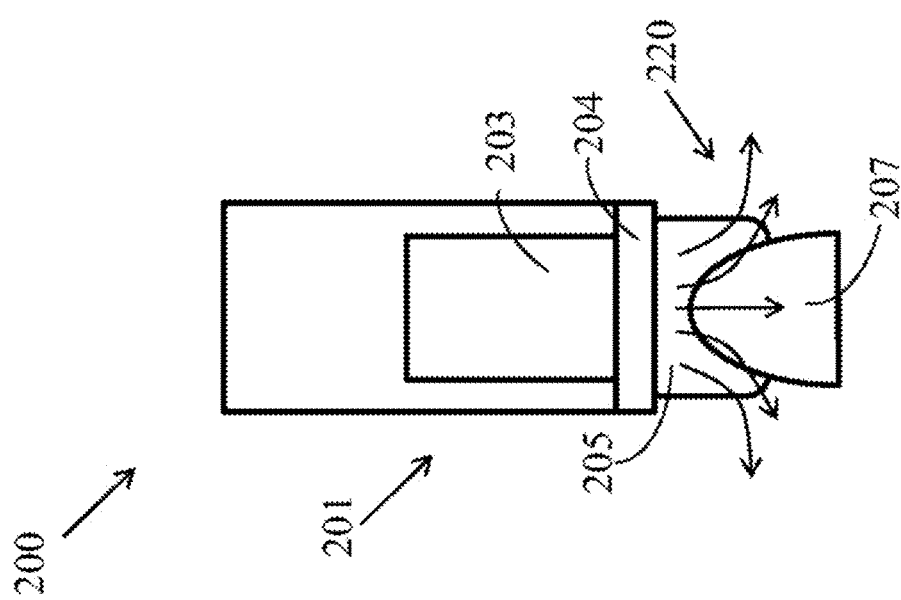
FIG. 2A illustrates a cross-section view of an exemplary skin treatment apparatus for trans-tissue substance delivery and depictions of the electric field associated with the generated plasma with a flat electrode.

FIG. 2A illustrates a cross-section view of an exemplary skin treatment apparatus 200 for trans-tissue substance delivery and depictions of the electric field associated with the generated plasma with a flat electrode. System 200 includes a plasma generator 201. Plasma generator 201 includes an electrode 203 with a flat plasma generating surface and a mating flat dielectric barrier 204. Plasma is generated by the plasma generator 201 in gap 205 above the contoured skin 207. Plasma creates electric field 220 in the skin 207. FIG. 2A shows a cross-section of the spatial penetration and distribution of the electric field 220 in the skin 207. The electric field 220 is relatively strong only in the portion of the contoured skin 207 closest to the electrode 203/dielectric 204 with relatively deep penetration into the skin 207. In areas where the gap 205 is greater, the electric field 220 is relatively weak, resulting in relatively shallow, non-uniform, or no penetration into the skin 207.

FIG. 2B illustrates a cross-section view of an exemplary skin treatment apparatus 200' for trans-tissue substance delivery and depictions of the electric field associated with the generated plasma with a contoured electrode. System 200' includes a similar plasma generator 201, but with a contoured electrode 203' and contoured dielectric barrier 204'. Plasma is generated by the plasma generator 201' in gap 205' above the contoured skin 207. FIG. 2B shows a cross-section of the spatial penetration and distribution of the electric field 220' in the skin 207. The electric field 220' created by the contoured electrode 203'/dielectric 204' is uniform throughout the contoured skin 207 with consistent and uniform penetration into the skin 207.

Figure 3B:
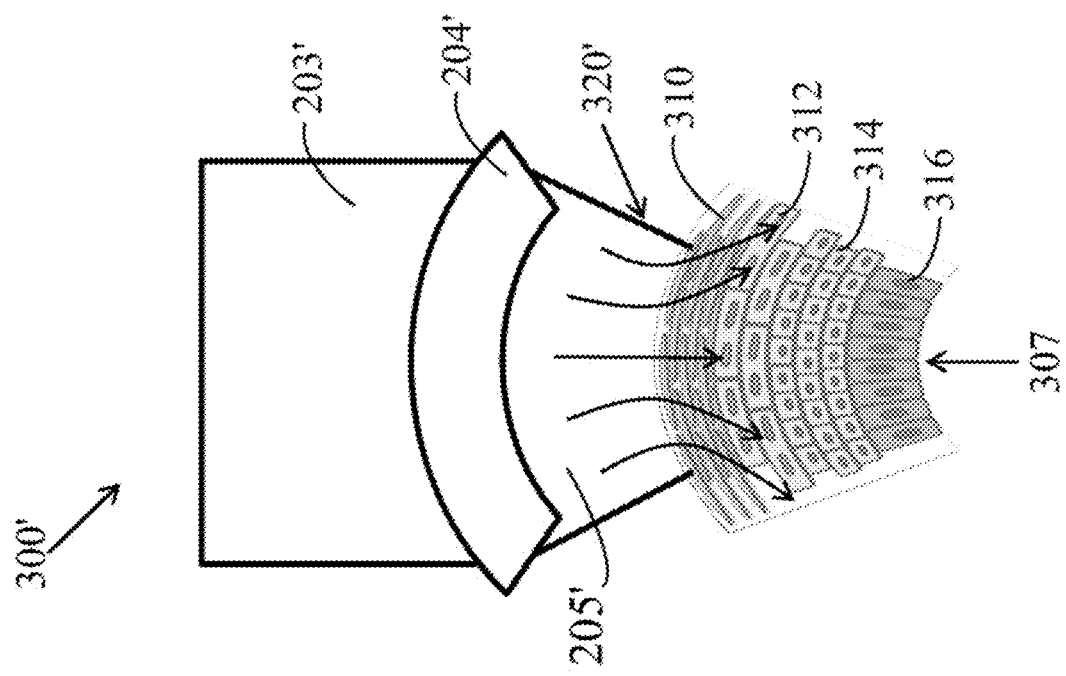
FIG. 3B illustrates an exemplary skin treatment apparatus for trans-tissue substance delivery with a contoured electrode depicting the associated respective electric field within a detailed cross-section view of skin.
Figure 3A:
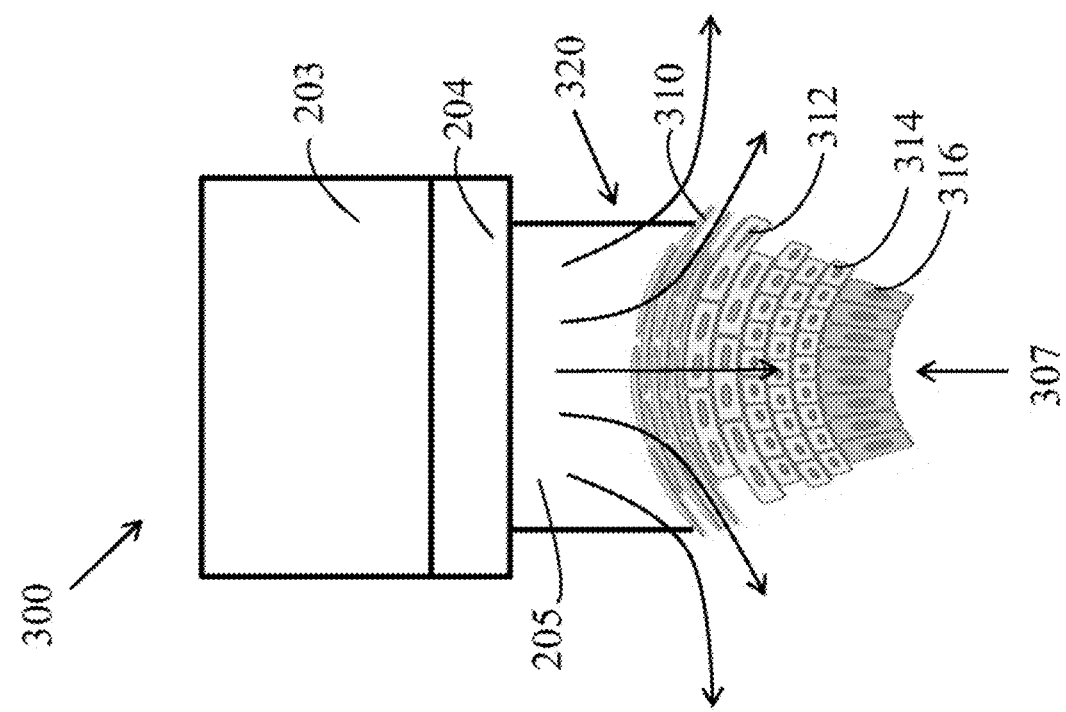
FIG. 3A illustrates an exemplary skin treatment apparatus for trans-tissue substance delivery with a flat electrode depicting the associated respective electric field within a detailed cross-section view of skin.

FIGS. 3A and 3B illustrate exemplary skin treatment apparatuses 300 and 300' for trans-tissue substance delivery (with flat and contoured electrode/dielectric systems, respectively) depicting the associated respective electric fields within a more detailed cross-section view of skin 307. Skin 307 is shown with various portions (layers) associated with intercellular and intracellular poration. These portions of skin 307 include the stratum corneum 310, viable epidermis 312, dermis 314, and subcutaneous tissue 316. In these figures, field lines 320, 320' depict the path of the electric field throughout the skin 307 with a flat electrode 203/ dielectric 204 system and a contoured electrode 203'/dielectric 204' system, respectively.

Thus, as illustrated in FIGS. 2A and 3A, with a flat electrode 203/dielectric 204, the electric field 220, 320 generated by the application of plasma on the skin 207, 307 in gap 205 has an inconsistent density of distribution and depth of permeation in the skin 207, 307, and the magnitude of the electric field 220, 320 is too weak and too strong in different portions the SC 310 and epidermis 312. As illustrated in FIGS. 2B and 3B, when a contoured electrode 203'/dielectric 204' is used, the electric field 220', 320' has a consistent density of distribution and depth of permeation in the skin 207, 307. Additionally, the magnitude of electric field 220', 320' is consistent in the SC 310 and epidermis 312, which is a typical target area for poration skin treatments, including, for example, to enhance transdermal drug delivery and intracellular uptake of drugs and molecules.

By using contoured electrodes and dielectrics, the electric field associated with the plasma can be controlled and directed through the targeted portions of contoured skin consistently. A contoured electrode and its associated electric field allows users to consistently target problem areas in contoured skin without adversely affecting non-target areas. Consistent spatial control of the depth and distribution of the electric field can increase the magnitude of the electric field in the targeted areas and decrease the magnitude of the electric field in the non-targeted areas.

Various tissue (e.g., skin) treatments include a desired (targeted) poration of the tissue to provide a desired rate of delivery of a selected substance (e.g., drugs, DNA, RNA, vaccines, proteins, molecules, macromolecules, etc.) after plasmaporation. Trans-tissue substance delivery can include topical, transdermal, and systemic deliveries and treatments, which can occur before, during, and/or after plasmaporation. Selective poration of the skin can target one or more portions of the skin and/or the surrounding tissue, including, for example, the stratum corneum, the epidermis, the blood stream, etc. Controlling the electric field generated in skin due to plasmaporation can be used to control the depth and distribution of permeation of a topically applied substance. Additionally, focusing the electric field in a targeted region of the skin or tissue selectively porates only that region of the skin or tissue needed to deliver the drug, thus localizing its effect.

Accordingly, the ability control the electric field of a trans-tissue substance delivery system using contoured electrodes and dielectrics can be combined with other plasma treatment parameters to control the delivery (e.g., depth of permeation) of a substance, including, for example, spacers, the type of plasma generator used, frequency, duty cycle, pulse duration, time of plasma treatment, time of application on the skin, etc.

Patient and user safety may also be improved due to the use of a conductive element (e.g., a grounded element), as discussed in more detail below, and a reduction in the current necessary to achieve the desired energy levels in the targeted areas. Also as discussed in detail below, the system can include a safety device, such as, for example, a position sensor, to ensure that the conductive element is in contact with the skin before plasma treatment begins. The system can also include a disposable contact surface associated with the conductive elements, such as, for example, a patch, to eliminate cross-contamination from patient to patient.

Spacers may be used to control the gap between the dielectric surface and the skin surface so that the gap between the dielectric surface and the skin surface is substantially consistent. Spacers may be used in embodiments where the skin surface is generally flat and/or when the skin surface is contoured. In some embodiments, one or more spacers can be applied to the skin for establishing the gap between the skin surface and the dielectric surface of a plasma generating device as the plasma generating device is positioned over the skin for the skin treatment. In other embodiments, one or more spacers can be applied to the plasma generating device before the skin treatment. In some embodiments, different, removable spaces may be used with the same plasma generating device for different skin treatments requiring different gaps between the between the dielectric and the skin. Adhesive may be used for securing the spacer to the skin and/or the plasma generating device.

In some embodiments, the spacer is made from a conductive material. In this manner, the spacer can also connect the skin to a circuit, including, for example, a ground, a bias voltage, or any other circuitry. In other embodiments, a separate conductive element may connect the skin to a circuit, including, for example, a ground, a bias voltage, or any other circuitry. In this manner, the electric field associated with the skin treatment may be better controlled and safer. For example, skin in circuit communication with a conductive element can avoid shocks and affect the electric field associated with the generated plasma, such that at least a portion of the electric field is directed through a region of the skin by the plasma and the conductive element. In some embodiments, circuitry can be configured to tune the characteristics of the electric field.

In other embodiments, a connection to circuitry or ground can be via a conductive patch attached to the skin and/or the plasma generating device. In some embodiments, the patch includes one or more spacers for providing the gap between the dielectric surface and the skin surface when the plasma generating device is placed in contact with skin via the conductive patch.

The spacers and/or conductive elements may be any shape suitable for a particular application. For example, a post or a ring shape may be used. In some embodiments, the spacer is adjustable to control the gap between the dielectric surface and the skin surface.

Figure 4B:
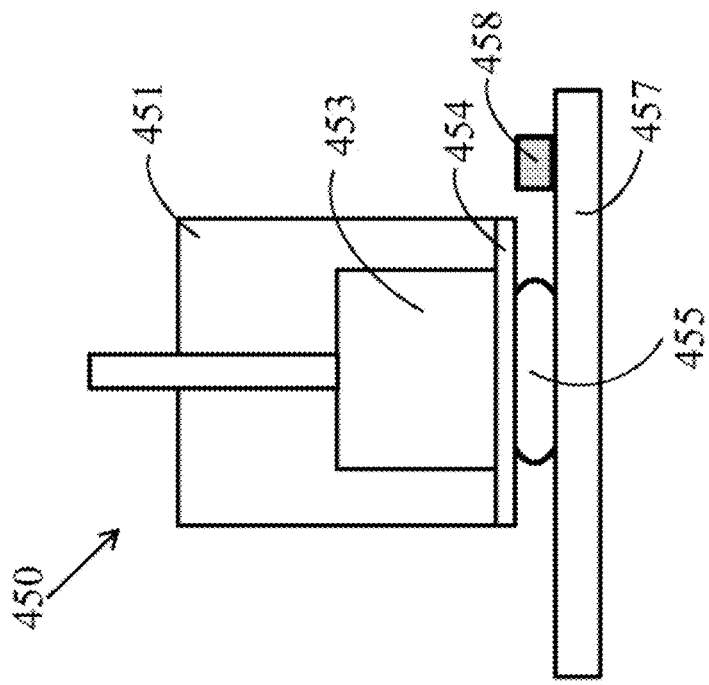
FIG. 4B illustrates a cross-section of another exemplary skin treatment system for trans-tissue substance delivery with a non-thermal DBD generator.
Figure 4A:
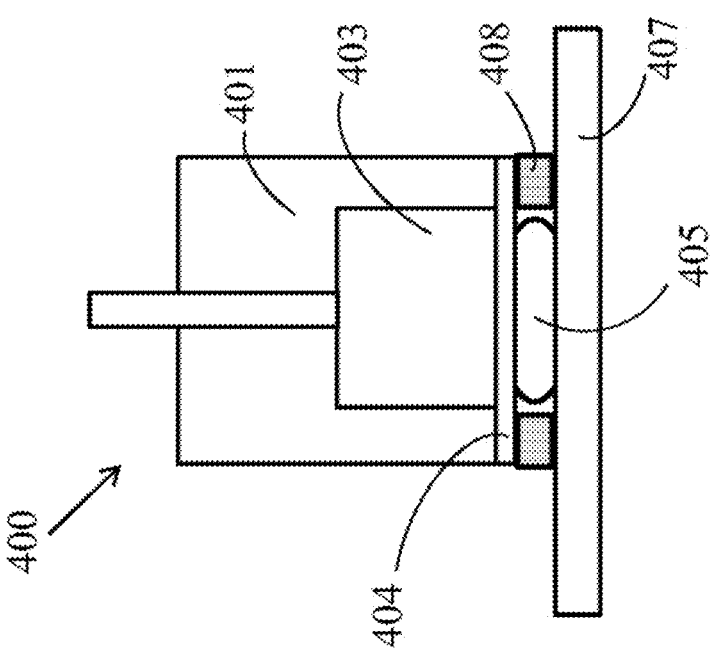
FIG. 4A illustrates a cross-section of an exemplary skin treatment system for trans-tissue substance delivery with a non-thermal DBD generator.

FIG. 4A illustrates a cross-section of an exemplary skin treatment system 400 for trans-tissue substance delivery with a non-thermal DBD generator. System 400 includes a plasma generator 401 integrated with an electrode 403 and a dielectric barrier 404 that creates a plasma 405 above skin 407. In system 400, a ring-shaped spacer/conductive element 408 is located between the skin 407 and the dielectric barrier 404 in a manner that surrounds the plasma 405 above the skin 407. The spacer/conductive element 408 controls the gap between the skin 407 and the electrode 403/dielectric barrier 404. The spacer/conductive element 408 may be attached to either the plasma generator 401 or the skin 407. The spacer/conductive element 408 may be in circuit communication with ground, associated circuitry, and/or other components (not shown), which may be integrated with the plasma generator 401 or separate.

In another embodiment, system 400 may also include a height-adjustment mechanism (not shown) associated with an integrated conductive element 408 such that the spacing between the plasma generator 401 and the conductive element 408 dictates the height of the plasma generator 401 above the skin 407. I.e., in this embodiment, when the conductive element 408 comes in contact with the skin 407, the plasma generator 401 will be the correct height above the skin 407. The plasma 405 creates an electric field (not shown) in a region of the skin 407.

FIG. 4B illustrates a cross-section of another exemplary skin treatment system 450 for trans-tissue substance delivery with a non-thermal DBD generator. System 450 includes a plasma generator 451 integrated with an electrode 453 and a dielectric barrier 454 that creates a plasma 455 above skin 457. Furthermore, in system 450, a block-shaped conductive element 458 is located on the skin 457 near the plasma 455. The conductive element 458 may be in circuit communication with ground, associated circuitry, and/or other components (not shown), which may be integrated with the plasma generator 451 or separate. The conductive element 458 may be placed on the skin 457 before the skin treatment.

In various embodiments, the conductive element 408, 458 may be permanent or temporary and reusable or disposable. An adhesive may be used to attach the conductive element 408, 458 to the plasma generating device 401, 451 or to the skin 407, 457.

In other embodiments, the conductive element 408, 458 makes contact with the skin 407, 457 via another conductive device, such as, for example, a conductive patch (not shown). The conductive patch may be attached to the conductive element or placed on the skin before the skin treatment. The conductive patch may have a shape that matches the shape of the conductive element that contacts the skin. For example, if the conductive element is ring-shaped, the conductive patch may have a ring shape about the same size as or slightly larger than the conductive element. In one embodiment, the conductive patch is cleanable, temporary, and/or disposable. In this manner, the conductive patch may be the only component of the skin treatment apparatus system that makes contact with the patient during the skin treatment. A conductive adhesive may be used to attach the conductive patch to the conductive element or to the skin. In some embodiments, the conductive patch comprises a releasable adhesive.

In various embodiments, the conductive element and/or the conductive patch may be configured for disposal after every use, after every patient, or according to some other regimen or protocol. In some embodiments, disposal includes discarding without any reuse. In other embodiments, the conductive element and/or the conductive patch may be reused, but configured for cleaning or sterilization after every use, after every patient, or according to some other regimen or protocol.

In some embodiments, a device may be used to sense and/or verify that the conductive element is in contact (circuit communication) with the skin before the plasma is generated. For example, the device may include a position sensor, a switch, a proximity sensor, a circuit check, or the like. This feature may be associated with a safety interlock system. The sensing device may be in circuit communication with a controller, such as, for example, controller 2150 shown in FIG. 21, where the controller controls (e.g., enables and disables) the plasma generating device based on an input or signal from the position sensing device. In another embodiment, the sensing device is a continuity circuit from the conductive element to the skin, e.g., by checking the resistance to ground. As discussed in more detail below, the sensing device can verify that the skin is grounded.

The conductive elements may be made of any conductive material (e.g., copper, aluminum, tungsten, silver, gold, titanium, palladium, conductive foam, conductive polymer, ITO, reticulated vitreous carbon, etc.). The conductive elements may be in many different forms (e.g. solid, liquid, gel, etc.). The conductive elements may be any shape suitable for an application, including planar shapes (i.e., the shape of the surface of the conductive element contacting the skin) and cross-sectional shapes. For example, the planar shape of the conductive element may be a straight line, a circle, an oval, a square, a rectangle, a donut, etc. The cross-sectional shape may be any shape suitable for providing sufficient contact with the skin.

In some embodiments, the top and bottom surfaces of the conductive element may be different. For example, the bottom surface may be configured or adapted to interface with the skin (e.g., for a good conductive surface-to-surface connection without connectors) and the top surface may be differently configured or adapted to interface with the plasma generating device (e.g., with an electrical connector, threaded connectors, etc.).

The conductive element may surround the plasma site or may be in close proximity to or adjacent to the plasma site. In some embodiments the conductive element includes a plurality of conductive elements. These elements may direct the electric field to different portions of the skin or may be used to more evenly distribute the electric field. In some embodiments, two or more conductive elements may form peripheries around the plasma site and may be arranged concentrically. In some embodiments the conductive element includes a plurality of segmented conductive elements. The segmented elements may exhibit the same features of non-segmented elements, including, for example, materials, overall shape, connections to other components, etc. In one embodiment, the segmented conductive elements are equally spaced and surround the plasma site.

The conductive element may have a size much larger than, slightly larger than, about the same size as the plasma treatment area. As discussed above, the conductive element may be secured to the skin (or any tissue) by having an adhesive backing or a conductive patch. In one embodiment, during storage, the adhesive backing can be sealed. During treatment, the adhesive backing can be exposed and placed in good contact with skin outside of or near the area to be plasma treated. Proper contact between the conductive element and the skin may be ensured before plasma treatment by a safety device as described above. The conductive element or an associated conductive patch may be integrated with, permanently attached to, or be a consumable item that temporarily attaches to the plasma generating device. A replaceable conductive element and/or conductive patch could eliminate cross contamination from one patient to another and also make cleaning components of the treatment apparatus easier between uses.

The conductive element may be floating, grounded, connected to a bias voltage, and/or connected to circuitry. In embodiments with more than one conductive element or segmented conductive elements, subsets of the conductive elements may be connected differently in any combination.

Figure 5B:
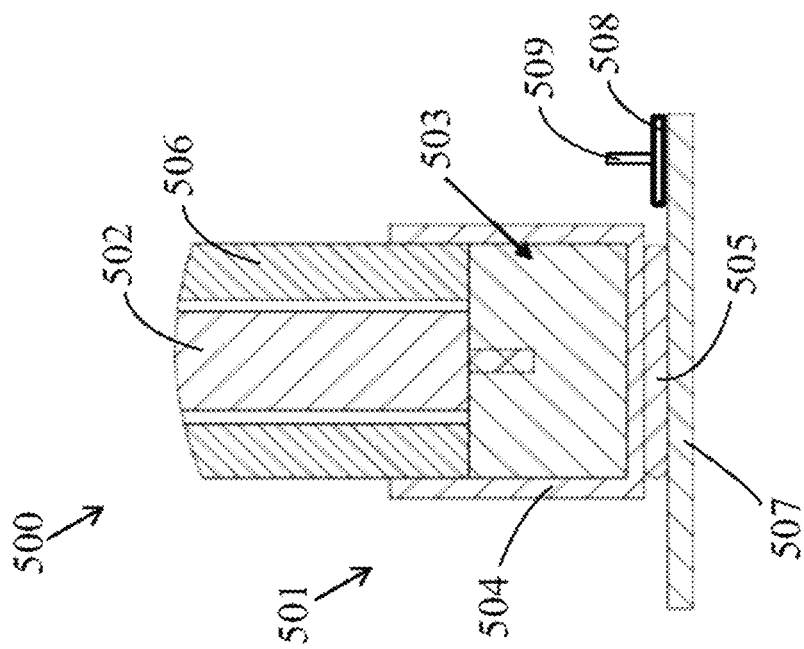
FIG. 5B is a cross-section drawing of the lower portion of the exemplary skin treatment apparatus shown in FIG. 5A.
Figure 5A:
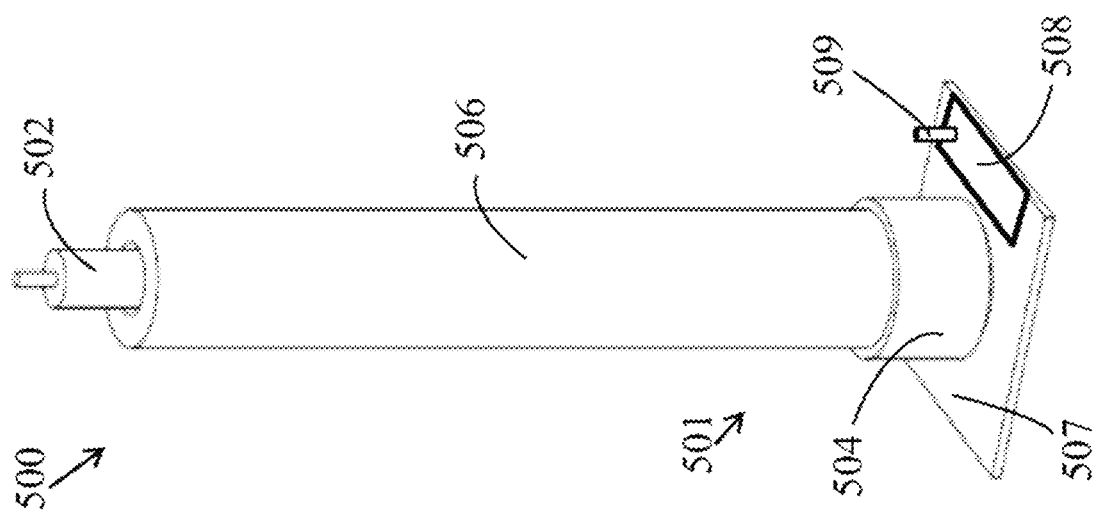
FIG. 5A is a drawing of an exemplary skin treatment apparatus for trans-tissue substance delivery.

FIG. 5A is a drawing of an exemplary skin treatment apparatus 500 for trans-tissue substance delivery. FIG. 5B is a cross-section drawing of the lower portion of the apparatus 500. Skin treatment apparatus 500 includes a plasma generator 501. Plasma generator 501 includes a high voltage cable 502 connected to an electrode 503 on a first end and a high voltage power supply (not shown) on the second end. The power supply and its associated circuitry and waveforms can be any of those mentioned above. The plasma generator 501 is a non-thermal DBD generator with a dielectric barrier 504 located along the sides and below the high voltage electrode 503. Plasma 505 can be generated between the dielectric barrier 504 and the skin 507. The high voltage electrode 503 and the dielectric barrier 504 can be located within a housing 506, along with additional components, as discussed above.

Plasma 505 is generated by the plasma generator 501 above skin 507 and can be in direct contact with the skin 507. In this embodiment, the apparatus 500 also incorporates an optional exemplary conductive element 508 that is also in contact with the skin 507. In this embodiment, the conductive element 508 is conductive tape located near the generated plasma 505. Also in this embodiment, a conductive connection post 509 attached to the conductive element 508 is shown for placing the conductive element 508 in circuit communication with circuitry (not shown, described above) associated with the conductive element 508. In one embodiment, circuitry may be integrated with the apparatus 500 or the power supply with connection post 509 facilitating the connection to the other circuitry, for example, using a cable or wire with suitable connectors. In one embodiment, the connection post 509 may be connected to ground, effectively grounding the conductive element 508 and the skin 507.

In some embodiments, a spacer (not shown) can also be used to determine a distance between the electrode 503 and the skin 507, including, for example, by use of a mechanical stop. Axial spacers can be adjustable so that the plasma air gap is adjustable. In other embodiments, the conductive element 508 and/or conductive connection post 509 can also be used as a spacer as discussed above.

In some embodiments, the dielectric barrier 504 is configured to be removable. In this manner, the dielectric barrier 504 is configured to be cleanable or disposable after every use. The dielectric barrier 504 can include an adhesive for securing the dielectric barrier 504 to the plasma generating device 501. The dielectric barrier 504 can also be attached to the electrode 503 surface. In this embodiment, the dielectric barrier 504 is configured as a removable cap that can be replaced, for example, after every use, after every patient, after a certain number of uses, etc.

In other embodiments a dielectric patch (not shown), with properties similar to the dielectric barrier, can be attached to a permanent dielectric barrier surface. The dielectric patch can have insulating properties similar to the dielectric 504, but with the convenience and functionality of being removable. In these embodiments, the dielectric 504 maintains a tight fit with the electrode 503 and provides a surface suitable for mating with the removable patch. The dielectric patch can be configured to be cleanable or disposable after every use. The dielectric patch can include an adhesive for securing the dielectric patch to the dielectric barrier 504. One embodiment of a dielectric patch includes a thin film barrier.

Figure 6B:
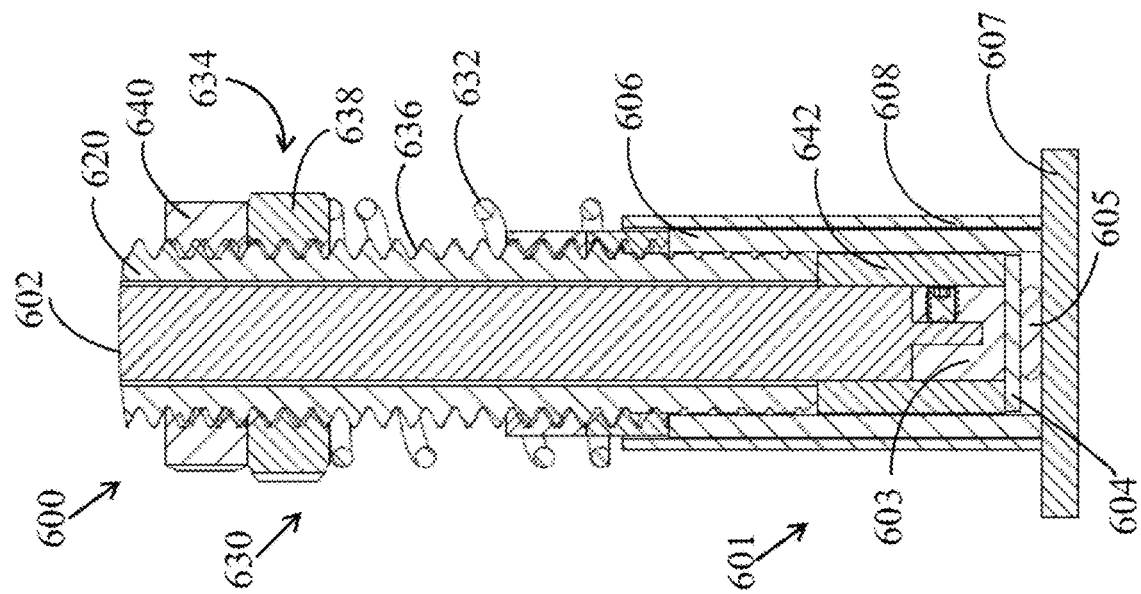
FIG. 6B is a cross-section drawing of the lower portion of the exemplary skin treatment apparatus shown in FIG. 6A.
Figure 6A:
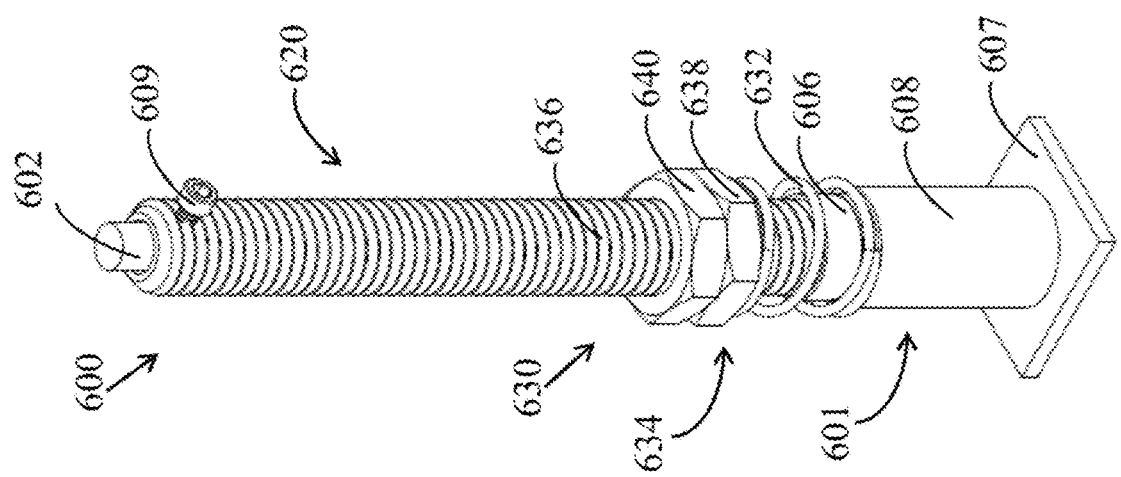
FIG. 6A is a drawing of another exemplary skin treatment apparatus for trans-tissue substance delivery.

FIG. 6A is a drawing of another exemplary skin treatment apparatus 600 for trans-tissue substance delivery. FIG. 6B is a cross-section drawing of the lower portion of the apparatus 600. Skin treatment apparatus 600 includes a plasma generator 601. Plasma generator 601 includes a high voltage cable 602 connected to an electrode 603 on a first end and a high voltage power supply (not shown) on the second end. The power supply and its associated circuitry and waveforms can be any of those mentioned above. The plasma generator 601 is a non-thermal DBD generator with a dielectric barrier 604 located below the high voltage electrode 603. Plasma 605 can be generated between the dielectric barrier 604 and the skin 607. Apparatus 600 is also shown with dielectric cylinder 606 that prevents plasma from occurring between the dielectric barrier 604 and the conductive element 608. This helps direct the plasma to the skin 607 rather than toward the conductive element 608. If conductive element 608 is adjusted vertically to change the plasma gap, the dielectric cylinder 606 can move with the conductive element 608. The high voltage electrode 603 and the dielectric barrier 604 can be located within a housing (e.g., comprising body 620 and/or other components), along with additional components, as discussed above.

Plasma 605 is generated by the plasma generator 601 above skin 607 and can be in direct contact with the skin 607. In this embodiment, the apparatus 600 also incorporates an exemplary conductive element 608 that is also in contact with the skin 607. In this embodiment, the conductive element 608 is cylindrical with a circular shape and surrounds the generated plasma 605. Also in this embodiment, a strain relief screw 609 is shown for securing the high voltage cable 602 within body 620. Circuitry (not shown, described above) associated with the conductive element 608 may be placed in circuit communication with the conductive element 608 via a conductive tab (not shown). In another embodiment, circuitry may be integrated with the apparatus 600. In another embodiment, a floating ground may be utilized by not connecting circuitry or a ground to the conductive element 608.

In this embodiment, the apparatus 600 also includes a spring-loaded mechanism 630 with a helical spring 632 that biases the conductive element 608 into proper contact with the skin 607. The conductive element 608 may be connected to ground or other circuitry via a tab or other connection means (not shown). The conductive element 608 can move axially. In operation, the apparatus 600 is placed in contact with the skin 607 with applied pressure such that the spring 632 of the spring-loaded mechanism 630 compresses to ensure that the conductive element 608 is in contact with the skin 607. In this manner, the spring-loaded mechanism 630 can provide the connection to circuitry or ground throughout a range of gaps between the dielectric 604 and the skin 607.

In some embodiments, the apparatus 600 includes a position sensing device (not shown) that changes state when the conductive element 608 contacts the skin 607 and compresses the spring 632 of the spring-loaded mechanism 630. For example, in one embodiment, the sensing device is a switch that closes when the conductive element 608 is in contact with the skin 607, indicating that the apparatus 600 is in a ready position, as discussed in detail above. In this embodiment, the spring-loaded mechanism 630 also includes an adjustable tension mechanism 634. In particular, the adjustable tension mechanism 634 includes a threaded shaft 636 on the body 620 with a corresponding nut 638 (and optional locking nut 640) that forms a stop against the spring 632. In some embodiments, the spring-loaded mechanism 630 can also be used as a spacer to determine a distance between the electrode 603 and the skin 607, including, for example, by use of a mechanical stop (not shown). The stop for can also be adjustable axially. In other embodiments, other tension-control or biasing mechanisms may be used as equivalents to the spring-loaded mechanism 630 and adjustable tension mechanism 634 for the same purpose. In some embodiments, additional dielectric material 642 can be used to separate the grounded conductors of the apparatus 600 and the high voltage electrode 603.

Figure 7B:
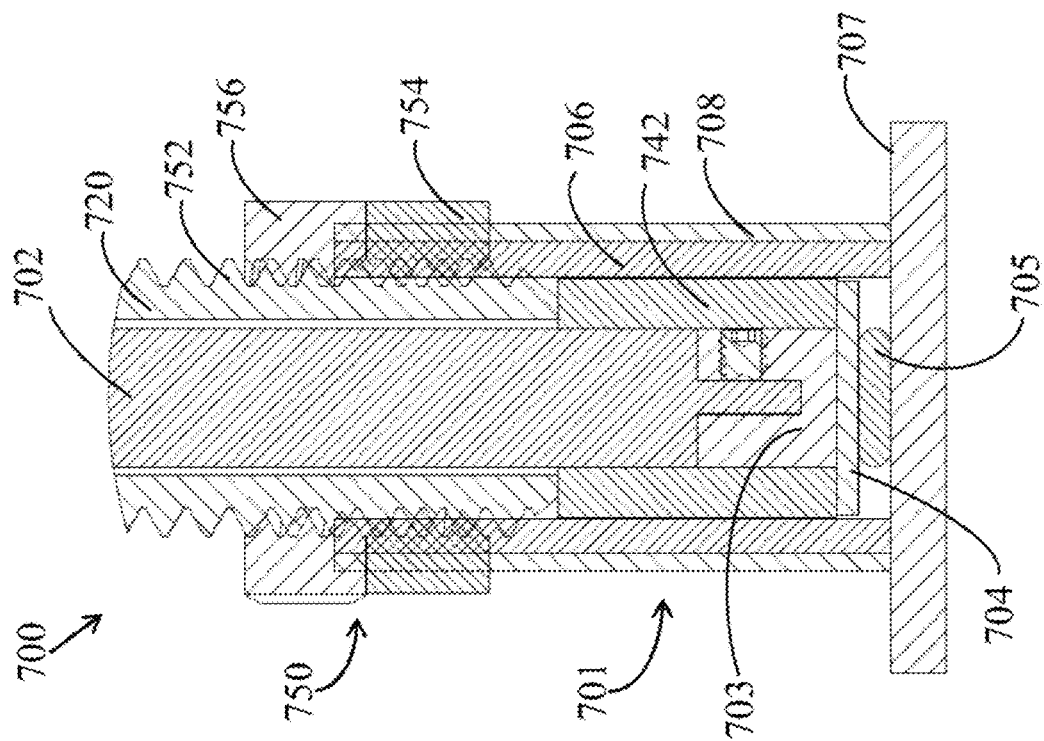
FIG. 7B is a cross-section drawing of the lower portion of the exemplary skin treatment apparatus shown in FIG. 7A.
Figure 7A:
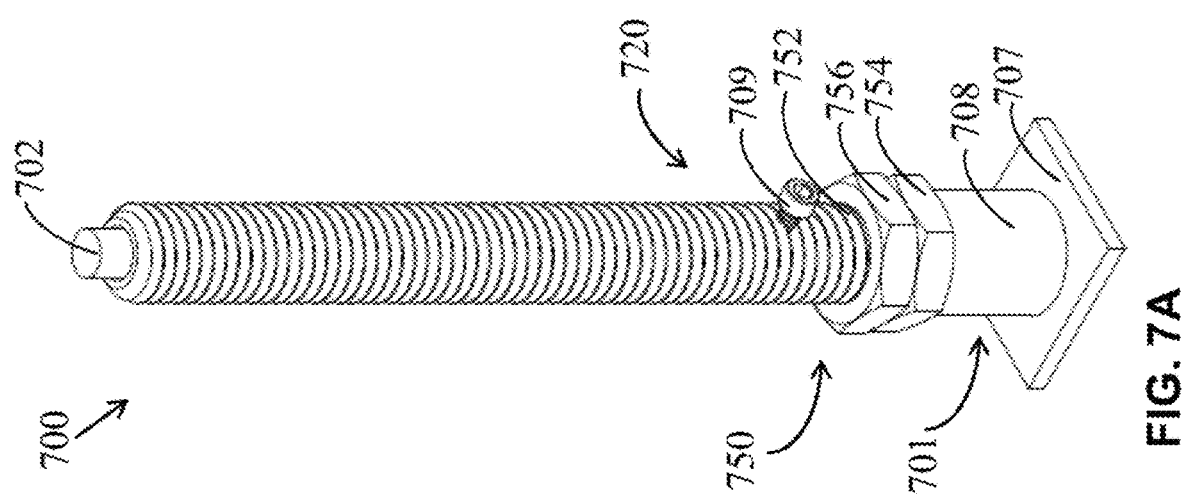
FIG. 7A is a drawing of another exemplary skin treatment apparatus for trans-tissue substance delivery.

FIG. 7A is a drawing of another exemplary skin treatment apparatus 700 for trans-tissue substance delivery. FIG. 7B is a cross-section drawing of the lower portion of the apparatus 700. Skin treatment apparatus 700 includes a plasma generator 701. Plasma generator 701 includes a high voltage cable 702 connected to an electrode 703. The plasma generator 701 is a non-thermal DBD generator with a dielectric barrier 704 located below the high voltage electrode 703.

Plasma 705 can be generated between the dielectric barrier 704 and the skin 707. Apparatus 700 is also shown with dielectric cylinder 706 that prevents plasma from occurring between the dielectric barrier 704 and the conductive element 708. This helps direct the plasma to the skin 707 rather than toward the conductive element 708. If conductive element 708 is adjusted vertically to change the plasma gap, the dielectric cylinder 706 can move with the conductive element 708. The high voltage electrode 703 and the dielectric barrier 704 can be located within a housing (e.g., comprising body 720 and/or other components), along with additional components, as discussed above. In some embodiments, additional dielectric material 742 can be used to separate the grounded conductors of the apparatus 700 and the high voltage electrode 703.

In this embodiment, the apparatus 700 also incorporates an exemplary conductive element 708 that surrounds the generated plasma 705. The conductive element 708 may be connected to ground or other circuitry via a tab or other connection means (not shown). A strain relief screw 709 is shown for securing the high voltage cable 702 within body 720. Circuitry (not shown, described above) associated with the conductive element 708 may be placed in circuit communication with the conductive element 708 via a conductive tab (not shown).

In this embodiment, the apparatus 700 also includes an adjustable height mechanism 750. In particular, the adjustable height mechanism 750 includes a threaded shaft 752 on the body 720 with a corresponding nut 754 (and optional locking nut 756) that forms a stop against the conductive element 708. In this manner, the adjustable height mechanism 750 is used to determine a pre-set distance between the electrode 703 and the skin 707 when the conductive element 708 is placed in contact with the skin 707.

FIG. 8A is a drawing of an exemplary skin treatment apparatus 800 for trans-tissue substance delivery on contoured skin surfaces. FIG. 8B is a cross-section drawing of the lower portion of the apparatus 800. Skin treatment apparatus 800 includes a plasma generator 801. Plasma generator 801 includes a high voltage cable 802 connected to an electrode 803 on a first end and a high voltage power supply (not shown) on the second end. The power supply and its associated circuitry and waveforms can be any of those mentioned above. The plasma generator 801 is a non-thermal DBD generator with a dielectric barrier 804 located below and alongside the high voltage electrode 803. Plasma can be generated across gap 805 between the dielectric barrier 804 and the skin 807. Apparatus 800 is also shown with dielectric cylinder 806 that prevents plasma from occurring between the dielectric barrier 804 and other components. The high voltage electrode 803 and the dielectric barrier 804 can be located within a housing (e.g., comprising body 820 and/or other components), along with additional components, as discussed above.

In this embodiment, the electrode 803 and dielectric barrier 804 are contoured with a radius that aligns with the contour of the skin 807 in the skin treatment area. This contouring will form a uniform air gap 805 between the skin 807 and the dielectric 804 in which uniform plasma can be created, as discussed in more detail above in relation to FIG. 1B. Plasma is generated by the plasma generator 801 in the gap 805 above skin 807 and can be in direct contact with the skin 807. A treatment substance 810 is shown in the target treatment area of the skin 807.

In this embodiment, the apparatus 800 also incorporates exemplary conductive elements 808 that are also in contact with the skin 807. In this embodiment, the conductive elements 808 are pins or posts that surround the plasma gap 805. Also in this embodiment, a height adjustment screw 809 is shown for controlling the position of the housing 806, which can be used to adjust the separation between the electrode 803 and the conductive elements 808. In this manner, different contoured surfaces can be treated with the same apparatus 800, for example, by manipulating the gap between the electrode 803 and the skin 807 in the axial direction.

In this embodiment, the body 820 and the conductive elements 808 are adjustable in the axial direction. In particular, the individual conductive elements 808 can be independently adjusted axially within the body 820 via locking screws 822 to further match the contour of various skin 807 contours.

Circuitry (not shown, described above) associated with the conductive elements 808 may be placed in circuit communication with the conductive elements 808 via a conductive tab (not shown). In another embodiment, circuitry may be integrated with the apparatus 800. In another embodiment, a floating ground may be utilized by not connecting circuitry or a ground to the conductive elements 808.

In this embodiment, the conductive elements 808 are spring-loaded with a spring (not shown) that biases the conductive elements 808 into contact with the skin 807. The conductive elements 808 can move axially. In operation, the apparatus 800 is placed in contact with the skin 807 with applied pressure such that the springs of the spring-loaded conductive elements 808 compress to ensure that the conductive elements 808 are in contact with the skin 807. In this manner, the spring-loaded conductive elements 808 can provide the connection to circuitry or ground throughout a range of gaps 805 between the dielectric 804 and the skin 807. This allows the operator to have various plasma air gaps 805 between the skin 807 and dielectric 804 and also reduces the possibility of losing the connection if the apparatus 800 is being held by hand, since the conductive elements 808 will compensate for any movement by the hand while holding the apparatus 800.

In some embodiments, the apparatus 800 includes a position sensing device (not shown) that changes state when the conductive elements 808 contacts the skin 807 and compresses the spring of the spring-loaded conductive elements 808. For example, in one embodiment, the sensing device is a switch that closes when one or more of the conductive elements 808 are in contact with the skin 807, indicating that the apparatus 800 is in a ready position, as discussed in detail above.

In some embodiments, the conductive elements 808 can also be used as a spacer to determine a distance between the electrode 803 and the skin 807, including, for example, by use of a mechanical stop (not shown). The stop for can also be adjustable axially. In other embodiments, separate spacers may be used.

Dielectric sleeves 842 can be used to surround the conductors connecting the conductive elements 808 to the body 820 such that only a small portion of exposed conductive material is exposed near the tips of the conductive elements 808. Dielectric material between the ground conductor and the high voltage electrode (conductor) can be used to prevent unwanted plasma from being formed between the two conductors in any air gap that may exist between them.

Figure 9B:
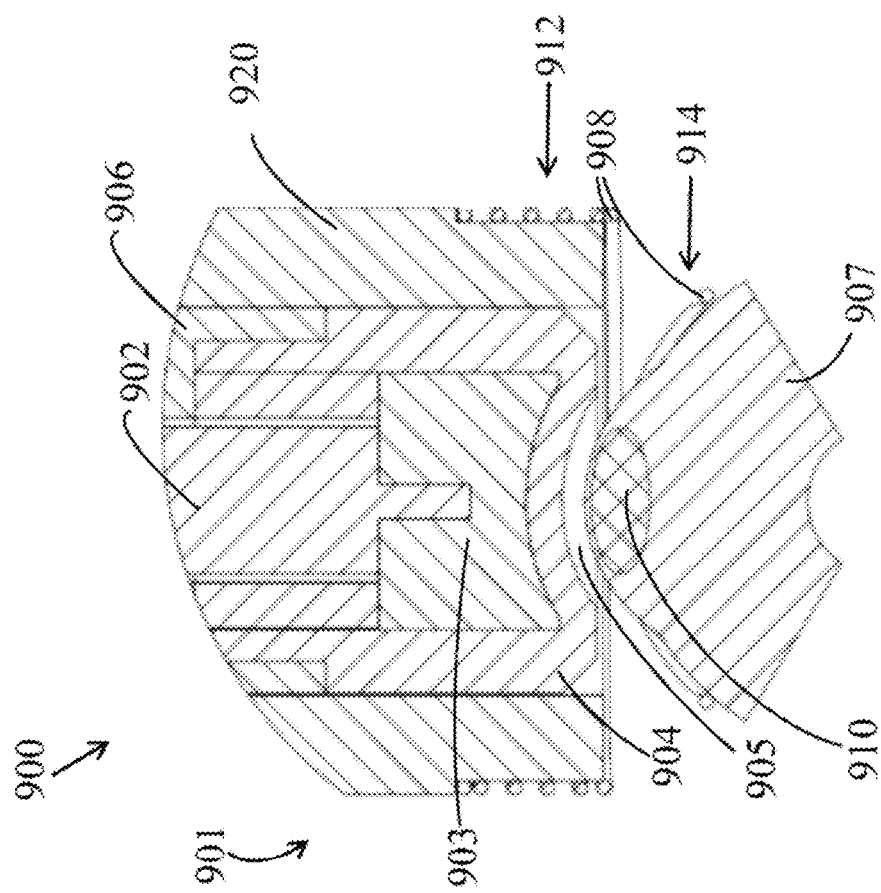
FIG. 9B is a cross-section drawing of the lower portion of the exemplary skin treatment apparatus shown in FIG. 9A.
Figure 9A:
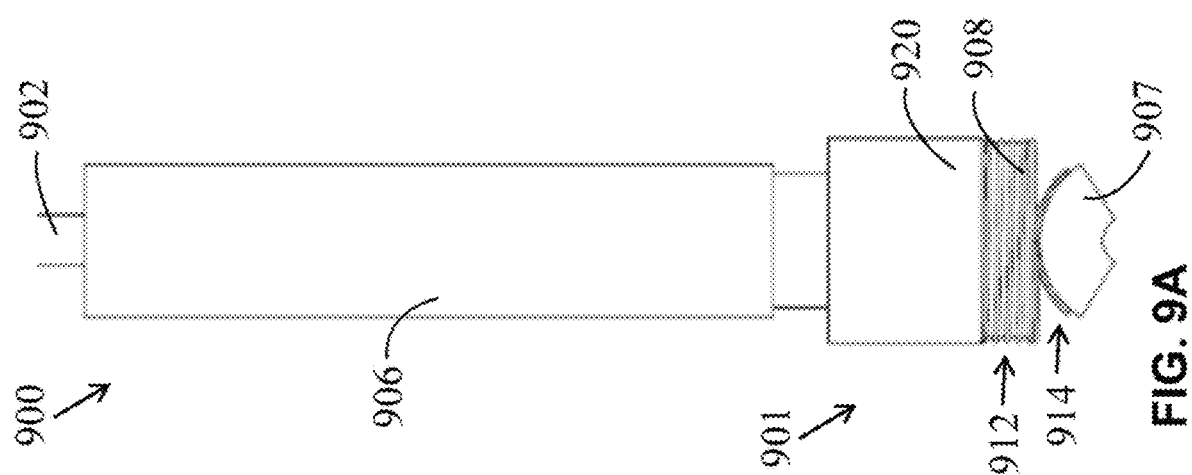
FIG. 9A is a drawing of another exemplary skin treatment apparatus for trans-tissue substance delivery on contoured skin surfaces.

FIG. 9A is a drawing of another exemplary skin treatment apparatus 900 for trans-tissue substance delivery on contoured skin surfaces. FIG. 9B is a cross-section drawing of the lower portion of the apparatus 900. Skin treatment apparatus 900 includes a plasma generator 901. Plasma generator 901 includes a high voltage cable 902 connected to an electrode 903 on a first end and a high voltage power supply (not shown) on the second end. The power supply and its associated circuitry and waveforms can be any of those mentioned above. The plasma generator 901 is a non-thermal DBD generator with a dielectric barrier 904 located below and alongside the high voltage electrode 903. Plasma can be generated across gap 905 between the dielectric barrier 904 and the skin 907. Apparatus 900 is also shown with dielectric cylinder 906 that prevents plasma from occurring between the dielectric barrier 904 and other components. The high voltage electrode 903 and the dielectric barrier 904 can be located within a housing (e.g., comprising body 920 and/or other components, along with additional components, as discussed above.

In this embodiment, the electrode 903 and dielectric barrier 904 are contoured with a radius that aligns with the contour of the skin 907 in the skin treatment area. This contouring will form a uniform air gap 905 between the skin 907 and the dielectric 904 in which uniform plasma can be created.

Plasma is generated by the plasma generator 901 in the gap 905 above skin 907 and can be in direct contact with the skin 907. A treatment substance 910 is shown in the target treatment area of the skin 907. In this embodiment, the apparatus 900 also incorporates exemplary conductive element 908 that is also in contact with the skin 907. In this embodiment, the conductive element 908 is wire that can act as a spring that surrounds the plasma gap 905. Circuitry (not shown, described above) associated with the conductive element 908 may be placed in circuit communication with the conductive element 908 via a tab or other connection means using any suitable connection (not shown). In another embodiment, circuitry may be integrated with the apparatus 900. In one embodiment, the conductive element 908 may be connected to ground. In another embodiment, a floating ground may be utilized by not connecting circuitry or a ground to the conductive element 908.

In this embodiment, the conductive element 908 is a spring that biases the conductive element 908 into contact with the skin 907. The conductive element spring 908 includes a helical portion 912 and a shaped or contoured portion 914. In the helical portion 912, the wire is wound in a helical fashion so that it provides the conductive element 908 with some spring. In the contoured portion 914, the wire is bent to conform to the shape of the skin 907. Both portions 912, 914 ensure solid uniform contact with the skin 907.

The conductive element 908 can move axially. In operation, the apparatus 900 is placed in contact with the skin 907 with applied pressure such that the spring of the conductive element 908 compresses to ensure that the conductive element 908 is in contact with the skin 907. In this manner, the conductive element 908 can provide the connection to circuitry or ground throughout a range of gaps 905 between the dielectric 904 and the skin 907. This allows the operator to have various plasma air gaps 905 between the skin 907 and dielectric 904 and also reduces the possibility of losing the connection if the apparatus 900 is being held by hand, since the conductive element 908 will compensate for any movement by the hand while holding the apparatus 900. In other embodiments, spacers may also be used.

Figure 11:
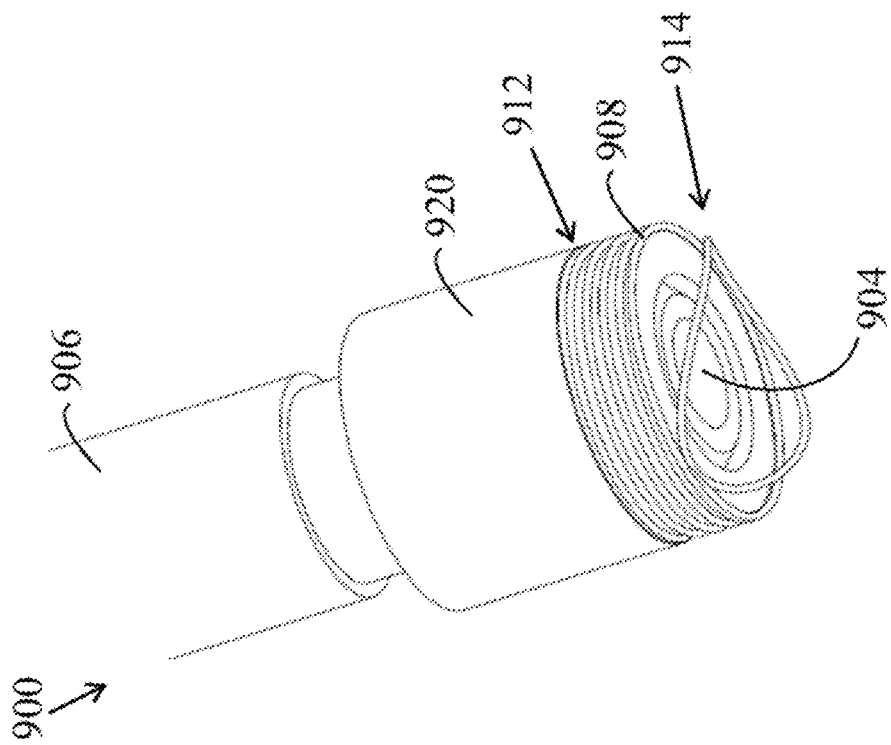
FIG. 11 is a drawing of the lower portion of the exemplary skin treatment apparatus shown in FIG. 9A showing the interface with the skin.
Figure 10:
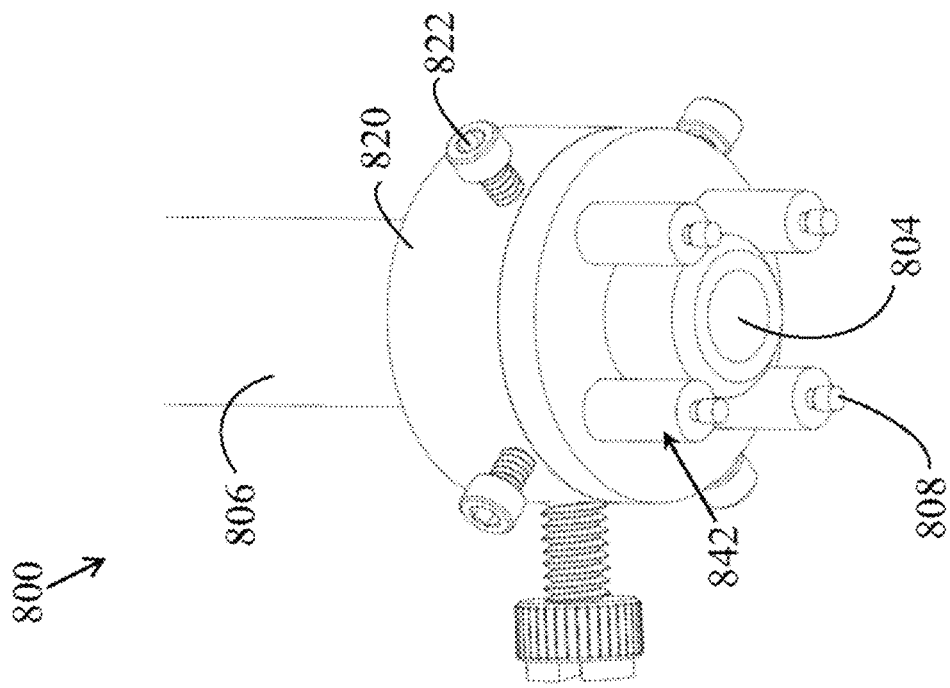
FIG. 10 is a drawing of the lower portion of the exemplary skin treatment apparatus shown in FIG. 8A showing the interface with the skin.

FIGS. 10 and 11 are drawings of the exemplary skin treatment apparatuses 800 and 900, respectively. These drawings show three-dimensional views of the portions of the apparatuses 800, 900 that interface with the skin 807, 907.

To provide further control of the delivery of substances as part of skin treatments, in other embodiments, the system can include a substance delivery device. The substance delivery device includes a substance reservoir for holding a treatment substance associated with the skin treatment. The treatment substance can be applied to the skin before and/or after the skin is exposed to plasma. In various embodiments, the substance reservoir can include a release device that may be actuated manually or automatically for applying the substance to the skin. In some embodiments, the plasma generating device includes a cavity for accepting the substance reservoir. The cavity can be configured to position an outlet of the substance reservoir proximate to the skin treatment area (e.g., in the center of or to the side of the skin treatment area) when the substance reservoir is positioned within the cavity. In some embodiments, the treatment substance can be applied to the skin through a hole in the high voltage electrode and/or a hole in a dielectric barrier of the plasma generating device.

Figure 12:
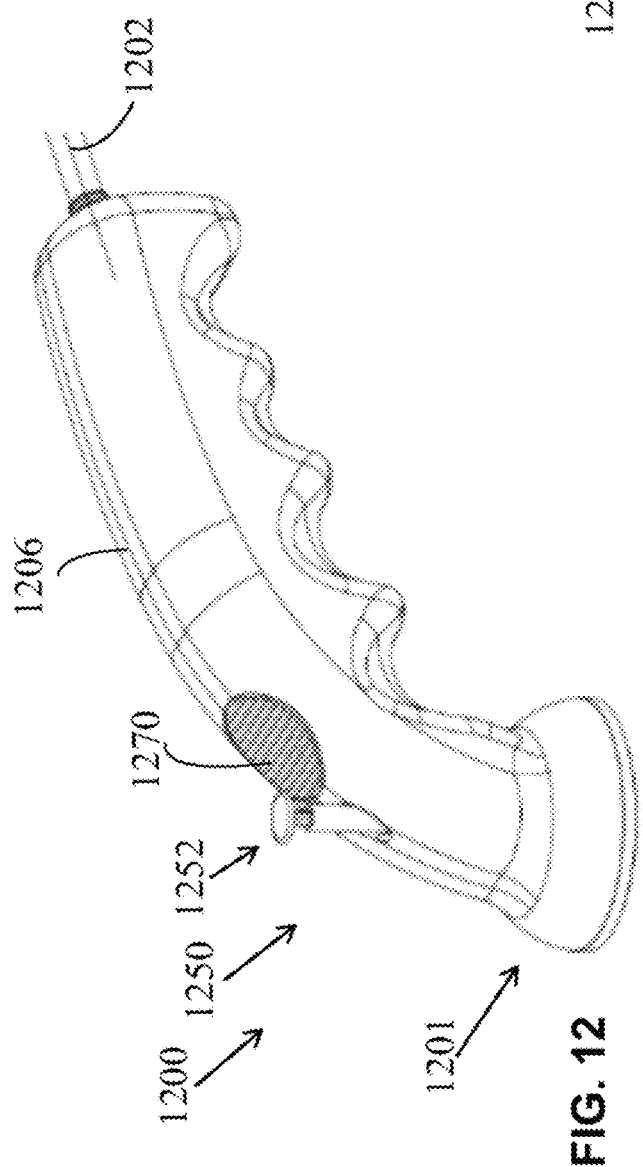
FIG. 12 is a drawing of an exemplary trans-tissue substance delivery apparatus with a substance delivery device.
Figure 13A:
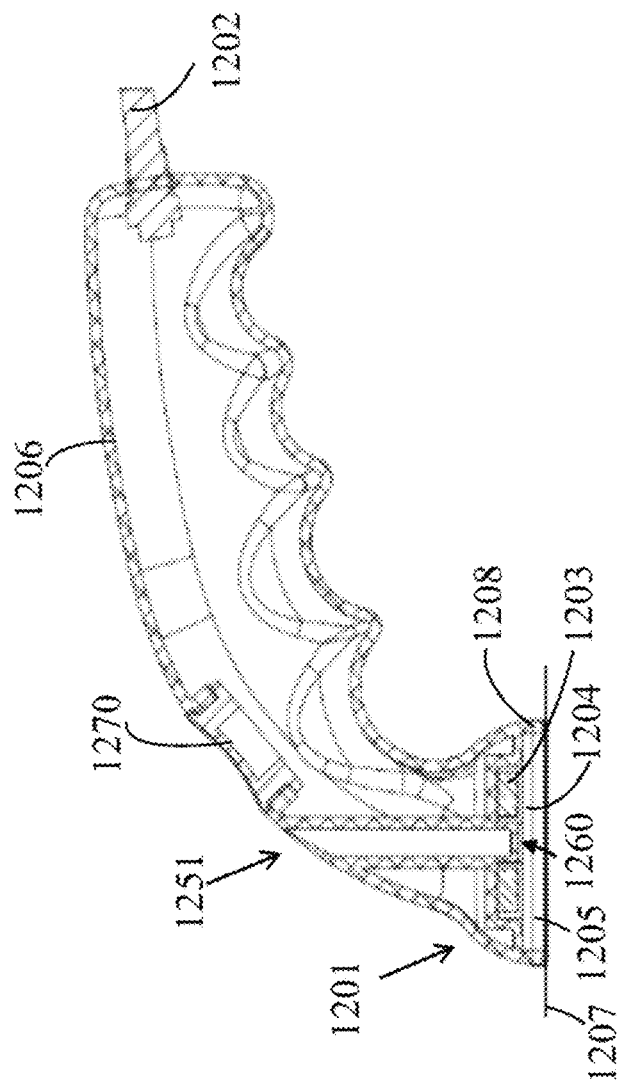
FIG. 13A is a cross-section drawing of the exemplary skin treatment apparatus shown in FIG. 12 with an empty cavity.

FIG. 12 is a drawing of an exemplary skin treatment apparatus 1200 with a substance delivery device. FIGS. 13A-13C show cross-section drawings of the apparatus 1200. Skin treatment apparatus 1200 includes a plasma generator 1201. Plasma generator 1201 includes a high voltage cable 1202 connected to a ring-shaped electrode 1203. The plasma generator 1201 is a non-thermal DBD generator with a dielectric barrier 1204 located below and along the sides of the high voltage electrode 1203. Plasma can be generated in gap 1205 between the dielectric barrier 1204 and the skin 1207. The high voltage electrode 1203 and the dielectric barrier 1204 can be located within a housing 1206, along with additional components, as discussed in the embodiments above. In this embodiment, the apparatus 1200 also incorporates a conductive element 1208 that surrounds the plasma gap 1205 when in contact with the skin 1207. The circuitry (not shown, described above) associated with the conductive element 1208 may be, for example, a grounding circuit.

Apparatus 1200 also includes a substance delivery device 1250. In this embodiment, the apparatus 1200 includes a cavity 1251 for accepting a substance reservoir 1252. The cavity 1251 is configured to position an outlet (e.g., tip) of the substance reservoir 1252 in the center of the skin treatment area when the substance reservoir 1252 is positioned within the cavity 1251. The substance delivery device 1250 includes substance reservoir 1252 for holding a treatment substance associated with the skin treatment. In this embodiment, the substance reservoir 1252 is a syringe. The substance reservoir 1250 includes a release device, which is a plunger 1254 configured to slide within a barrel 1256 of the syringe 1252 to expel the treatment substance from a tip 1258 of the syringe 1252. In this embodiment, the plunger 1254 is actuated manually to apply the substance to the skin 1207 through a hole 1260 in the center of the ring-shaped electrode 1203.

FIGS. 13A-13C show the steps associated with using the substance delivery device 1250. In particular, FIG. 13A shows the apparatus 1200 with an empty cavity 1251 before the syringe 1252 is positioned into the cavity 1251. FIG. 13B shows the apparatus 1200 with the syringe 1252 placed into the cavity 1251 before the plunger 1254 is actuated. In this manner, the tip 1258 of the syringe 1252 is positioned into the hole 1260 in the center of the ring-shaped electrode 1203, above the skin 1207 to be treated. The syringe 1252 may be placed into the cavity 1251 before, during, or after the plasma is generated. FIG. 13C shows the apparatus 1200 with plunger 1254 actuated to expel the treatment substance from a tip 1258 of the syringe 1252 onto the skin 1207 in the area exposed to the plasma. The plasma generating device 1201 may generate plasma before, during, and/or after the treatment substance is applied to the skin 1207. In some embodiments, the apparatus can include a trigger or button 1270 for actuating the plasma generating device 1201.

Figure 14B:
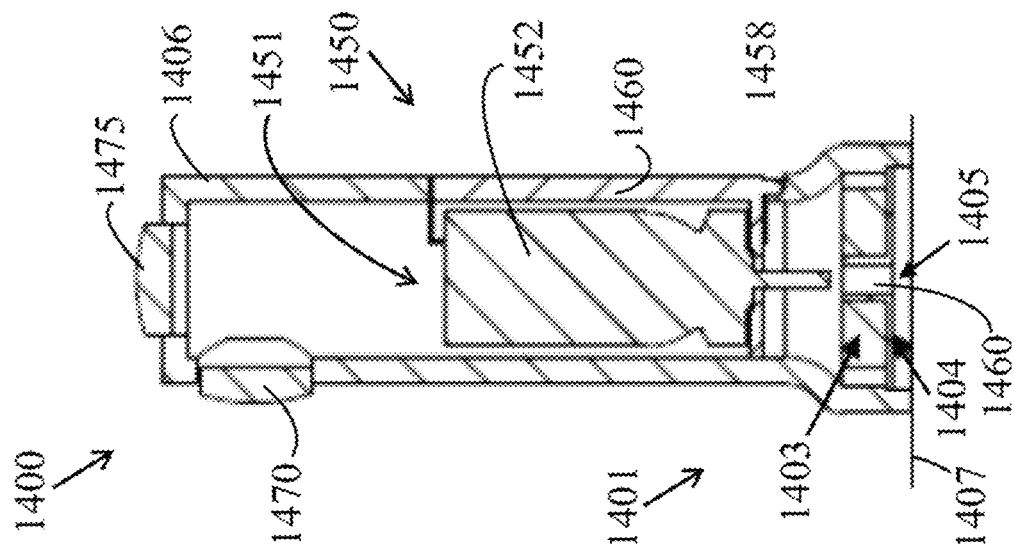
FIG. 14B is cross-section drawing of the exemplary skin treatment apparatus shown in FIG. 14A.
Figure 14A:
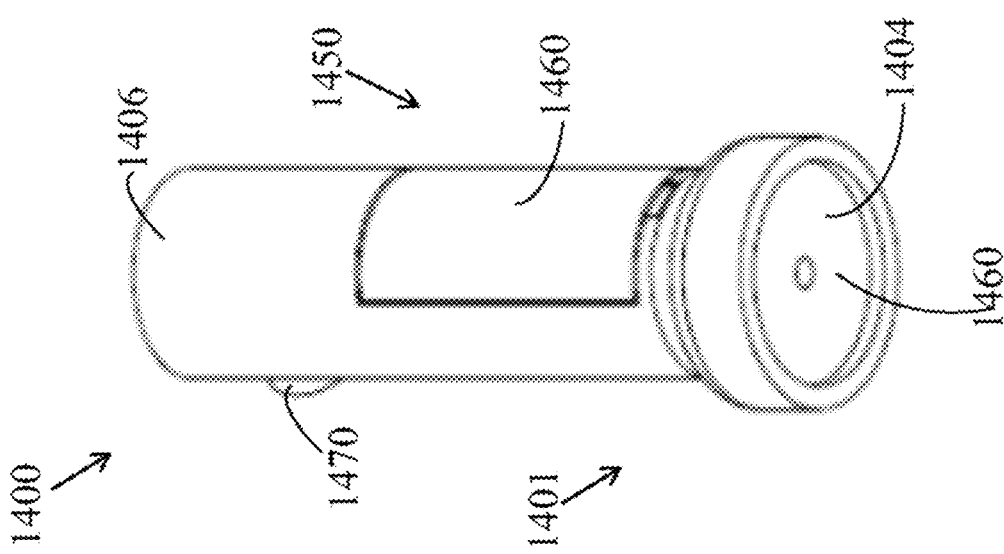
FIG. 14A is a drawing of another exemplary skin treatment apparatus with a substance delivery device.

FIG. 14A is a drawing of another exemplary skin treatment apparatus 1400 with a substance delivery device. FIG. 14B is a cross-section drawing of the apparatus 1400. Skin treatment apparatus 1400 includes a plasma generator 1401. Plasma generator 1401 may be battery-powered and includes a ring-shaped electrode 1403. The plasma generator 1401 is a non-thermal DBD generator with a dielectric barrier 1404 located below and along the sides of the high voltage electrode 1403. Plasma can be generated in gap 1405 between the dielectric barrier 1404 and the skin 1407. The high voltage electrode 1403 and the dielectric barrier 1404 can be located within a housing 1406, along with additional components, as discussed in the embodiments above. In another embodiment, the apparatus 1400 may incorporate a conductive element (not shown) that surrounds the plasma gap 1405 when in contact with the skin 1407. Circuitry (not shown, described above) associated with the conductive element may be, for example, a grounding circuit.

Apparatus 1400 also includes a substance delivery device 1450. In this embodiment, the apparatus 1400 includes a cavity 1451 for accepting a substance reservoir 1452. The cavity 1451 is configured to position an outlet (e.g., tip) of the substance reservoir 1452 in the center of the skin treatment area when the substance reservoir 1452 is positioned within the cavity 1451. The substance delivery device 1450 includes substance reservoir 1452 for holding a treatment substance associated with the skin treatment. In this embodiment, the substance reservoir 1452 is a pressurized capsule. The substance reservoir 1450 includes a release device, which can be, for example, a valve (not shown) configured to allow the treatment substance to exit a tip 1458 of the capsule 1452. In various embodiments, the release device may be a separate device or may be integrated into the apparatus 1400 or the substance reservoir 1452. In this embodiment, the release device is actuated automatically to release the substance onto the skin 1407 through a hole 1460 in the center of the ring-shaped electrode 1403. In another embodiment, the release device may be actuated manually. For example, the release device may be a valve that can be actuated electronically by a signal from a button (e.g., button 1475) or a controller, or the release device may be a valve that can be actuated manually by applying pressure to the top of the capsule 1452 or tip 1458.

Figure 15C:
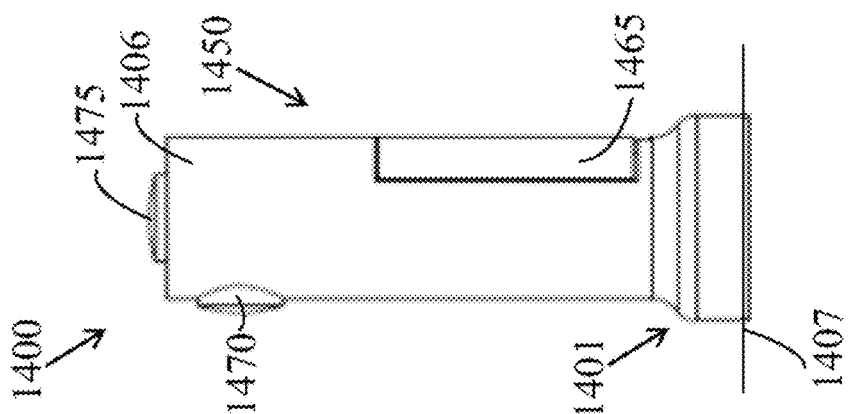
FIG. 15C is a drawing of the exemplary skin treatment apparatus shown in FIG. 14A with the door closed.
Figure 15B:
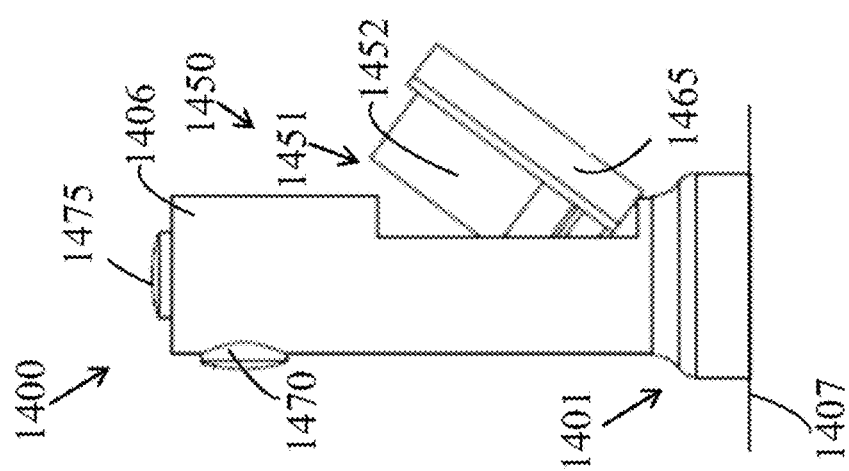
FIG. 15B is a drawing of the exemplary skin treatment apparatus shown in FIG. 14A with a capsule placed into the door.
Figure 15A:
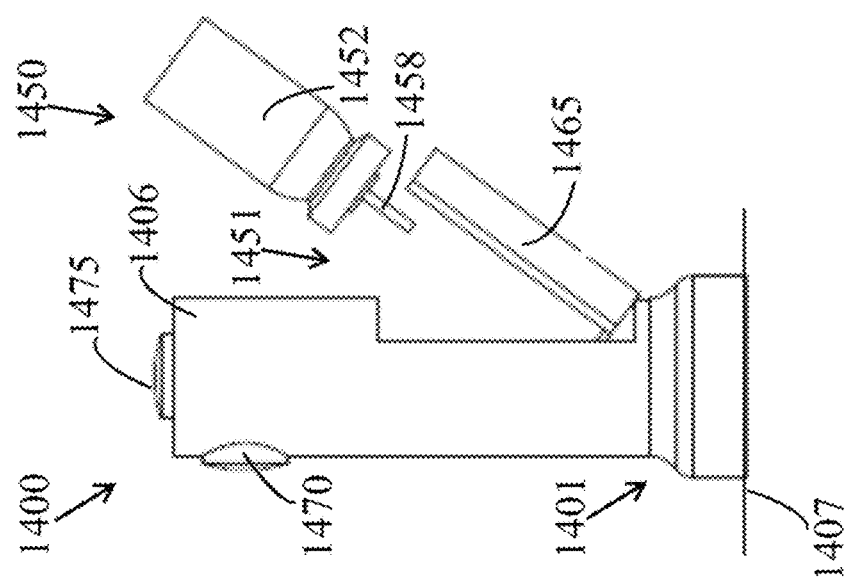
FIG. 15A is a drawing of the exemplary skin treatment apparatus shown in FIG. 14A with an open door.

FIGS. 15A-15C show the steps associated with using the substance delivery device 1450. In particular, FIG. 15A shows the apparatus 1400 with an open door 1465 exposing an empty cavity 1451 before the capsule 1452 is positioned into the cavity 1451. The door 1465 can be configured to open to accept the capsule 1452 into the cavity and configured to close to secure the capsule 1452 into the cavity. FIG. 15B shows the apparatus 1400 with the capsule 1452 placed into the door 1465 before the door 1465 closed. FIG. 15C shows the apparatus 1400 with the door 1465 is closed. In this manner, the tip 1458 of the capsule 1452 is positioned above the hole 1460 in the center of the ring-shaped electrode 1403, above the skin 1407 to be treated. In this embodiment, the capsule 1452 is placed into the cavity 1451 before the plasma is generated. The plasma generating device 1401 may generate plasma before, during, and/or after the treatment substance is applied to the skin 1407.

In this embodiment, the apparatus 1400 includes a trigger or button 1470 for actuating the plasma generating device 1401 and a trigger or button 1475 for actuating the substance delivery device 1450. In another embodiment, one control button can be used to initiate the skin treatment process, where the skin treatment process includes automatically generating the plasma for a first predetermined duration and automatically actuating the release device for a second predetermined duration to introduce the treatment substance to the skin. In another embodiment, the skin treatment process also includes automatically generating the plasma for a third predetermined duration after the treatment substance is introduced to the skin.

In other embodiments, a plasmaporation device and/or a substance delivery device may be configured as a skin treatment patch. The patch may be flexible enough to conform to the contours of the skin that the patch is applied to. In some embodiments, a plasmaporation device and a substance delivery device may be combined into a single skin treatment patch. In this embodiment, the treatment patch can include one or more of the elements and/or devices associated with the apparatuses mentioned above, for example, in relatively thin, layered forms. For example, the treatment patch can include layers for components of both a plasmaporation device and a substance delivery device. The substance delivery device includes a substance reservoir for holding a treatment substance associated with the skin treatment. The treatment substance can be applied to the skin before and/or after the skin is exposed to plasma. In various embodiments, the substance reservoir can include a release device that may be actuated manually or automatically for applying the substance to the skin. The substance reservoir can be configured to position an outlet proximate to the skin treatment area (e.g., in the center of or to the side of the skin treatment area).

In some embodiments, the treatment substance can be applied to the skin through a hole in the high voltage electrode and/or a hole in a dielectric barrier of the plasma generating device. In various embodiments, these holes may be pre-existing or may be created after plasmaporation (e.g., by piercing or puncturing the appropriate layers of the patch). In other embodiments, the treatment substance can be applied to the skin by removing the high voltage electrode, the dielectric barrier, and/or other components of the plasma generating portion of the skin treatment patch.

Figure 16A:
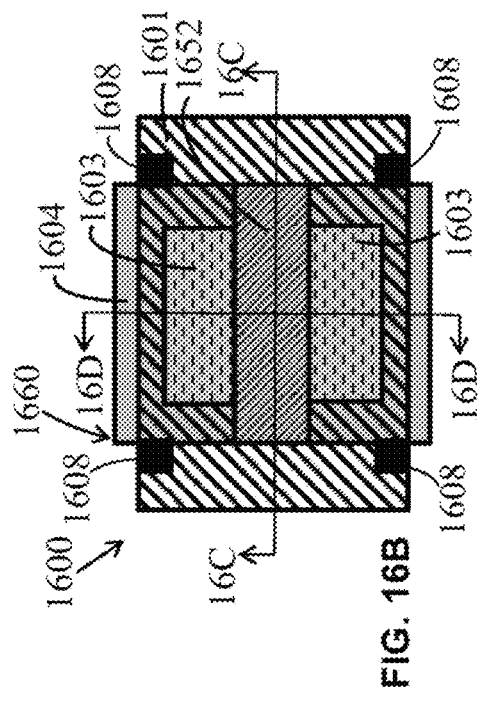
FIG. 16A is a drawing of a top view of an exemplary skin treatment patch with a substance delivery device.
Figure 16B:
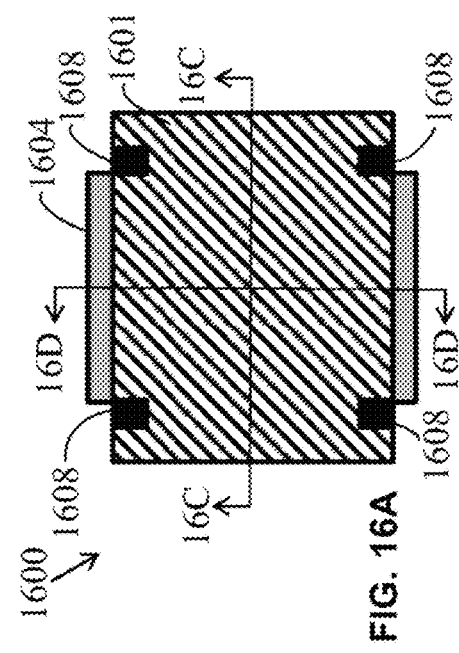
FIG. 16B is a drawing of a bottom view of the exemplary skin treatment patch shown in FIG. 16A.
Figure 16C:
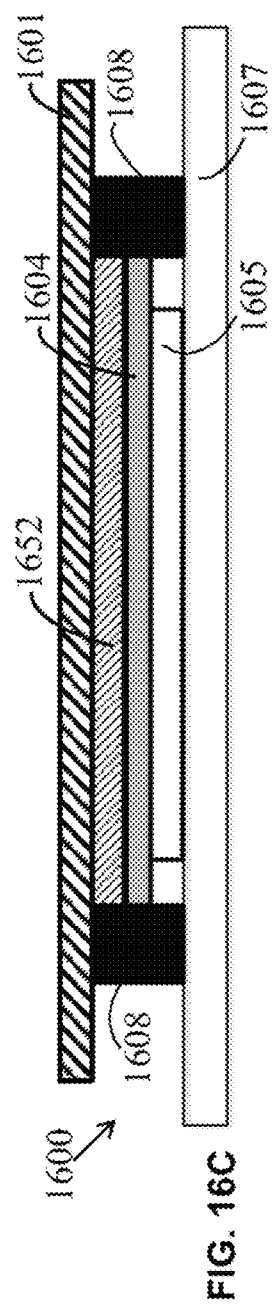
FIG. 16C is a drawing of a cross-section view of the exemplary skin treatment patch shown in FIG. 16A.
Figure 16D:
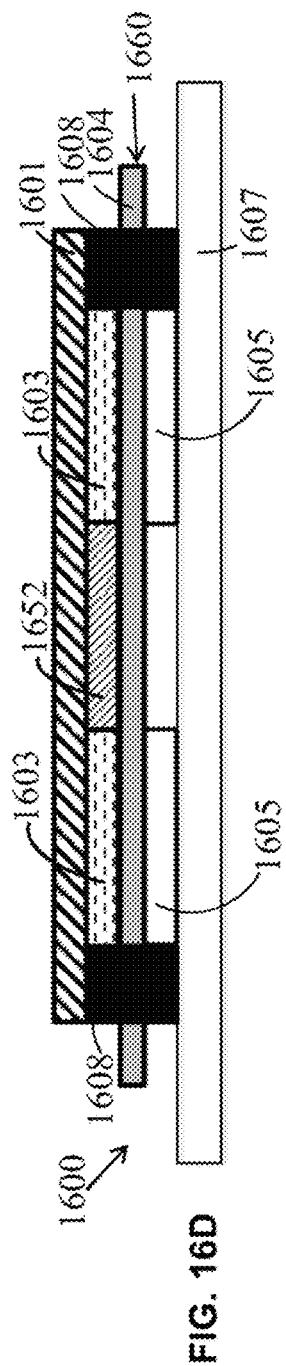
FIG. 16D is a drawing of another cross-section view of the exemplary skin treatment patch shown in FIG. 16A.

FIGS. 16A-16D are drawings of an exemplary skin treatment patch 1600 with a substance delivery device. FIG. 16A is a top view of the patch 1600; FIG. 16B is a bottom view (skin side) of the patch 1600; and FIGS. 16C-16D are cross-section drawings of the patch 1600 as shown. Treatment patch 1600 includes a substrate layer 1601. The substrate layer 1601 may be any material suitable for supporting the other layers and components of the patch 1601, including, for example, connections to other circuits (e.g., power supply, ground, communication signals, etc.) (not shown). Patch 1600 includes a high voltage electrode 1603 and a dielectric barrier 1604 located below the electrode 1603, which are associated with a non-thermal DBD plasma generator. Plasma 1605 can be generated in the gap between the dielectric barrier 1604 and the skin 1607. Patch 1600 also includes spacers 1608 to establish the proper gap between the dielectric barrier 1604 and the skin 1607. The spacers 1608 may be adjustable. Releasable adhesive (not shown) may also be used to adhere the spacers to the skin 1607.

Patch 1600 also includes a treatment substance reservoir 1652. The treatment substance reservoir 1652 is configured to position an outlet of the substance reservoir 1652 proximate to the skin treatment area. The substance reservoir 1652 holds a treatment substance associated with the skin treatment. In this embodiment, the substance reservoir 1652 is a space created between the substrate layer 1601 and dielectric barrier 1604, adjacent to the electrode 1603. In some embodiments, the treatment substance may be encapsulated in a cell placed between the substrate layer 1601 and dielectric barrier 1604.

In this embodiment, the dielectric barrier 1604 is removable from the patch 1600. In this manner, the dielectric barrier 1604 functions as a cover and/or the release device for the substance reservoir 1652. In particular, the dielectric barrier 1604 can be removed from the patch 1600 by pulling on a tab end 1660 of the dielectric barrier 1604 to peel the dielectric barrier 1604 away from the electrode 1603 and the substance reservoir 1652, allowing the treatment substance to be applied to the skin 1607. In other embodiments, other techniques may be used to expose the treatment substance to the skin 1607, including, for example, creating or exposing a hole in the bottom of the dielectric barrier 1604, removing a thin film covering the substance reservoir 1652, piercing or punching a hole into the dielectric barrier 1604 from above the patch 1600 (including, e.g., through the substrate layer 1601), squeezing or applying pressure to the patch 1600 to rupture the substance reservoir 1652, etc. In other embodiments, removing the dielectric barrier 1604 also removes the electrode 1603 and/or spacers 1608. Removing the electrode 1603 and/or spacers 1608 may allow for better contact between the treatment substance and the skin 1607. In another embodiment, the treatment patch may also include microneedles to porate the skin or deliver the treatment substance to the skin.

Figure 17:
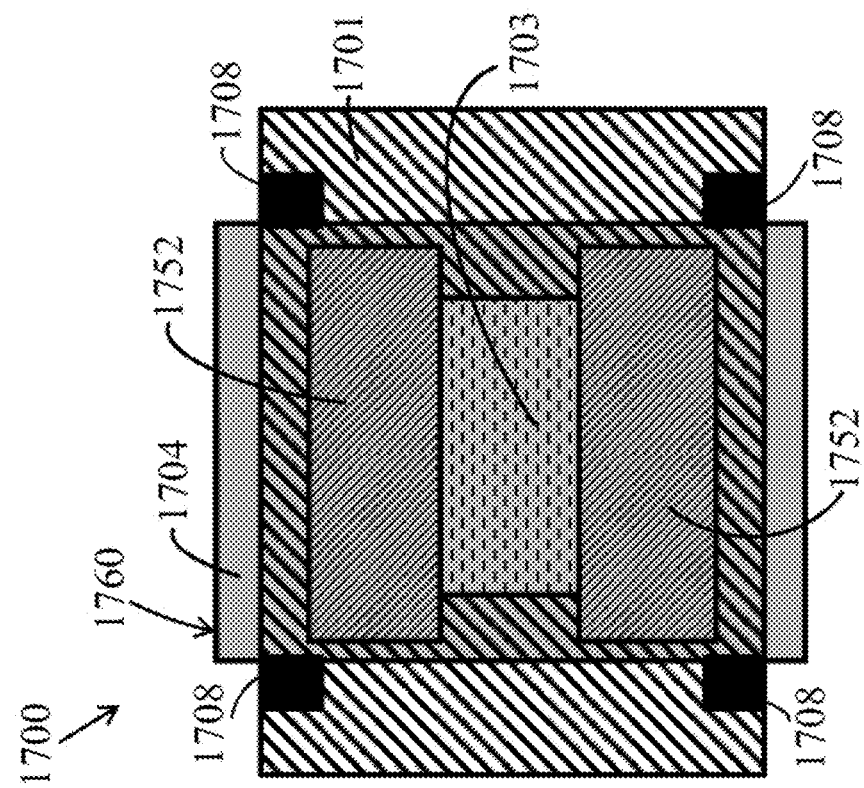
FIG. 17 is a drawing of a bottom view of another exemplary treatment patch with a substance delivery device.

FIGS. 17-20 are drawings of various other exemplary treatment patches. FIG. 17 is a drawing of a bottom view (skin side) of another exemplary treatment patch 1700 with a substance delivery device. Treatment patch 1700 is configured similarly to patch 1600, but with a different arrangement of the electrode and substance reservoir portions. Treatment patch 1700 includes a substrate layer 1701. The substrate layer 1701 may be any material suitable for supporting the other layers and components of the patch 1701, including, for example, connections to other circuits (e.g., power supply, ground, communication signals, etc.) (not shown). Patch 1700 includes a high voltage electrode 1703 and a dielectric barrier 1704 located below the electrode 1703, which are associated with a non-thermal DBD plasma generator. Patch 1700 also includes spacers 1708 to establish the proper gap between the dielectric barrier 1704 and the skin (not shown). The spacers 1708 may be adjustable.

Patch 1700 also includes a treatment substance reservoir 1752. The treatment substance reservoir 1752 is configured to position an outlet of the substance reservoir 1752 proximate to the skin treatment area. The substance reservoir 1752 holds a treatment substance associated with the skin treatment. In this embodiment, the substance reservoir 1752 is a space created between the substrate layer 1701 and dielectric barrier 1704, adjacent to each side of the electrode 1703. In some embodiments, the treatment substance may be encapsulated in a cell placed between the substrate layer 1701 and dielectric barrier 1704.

In this embodiment, the dielectric barrier 1704 is removable from the patch 1700. In this manner, the dielectric barrier 1704 functions as a cover and/or the release device for the substance reservoir 1752. In particular, the dielectric barrier 1704 can be removed from the patch 1700 by pulling on a tab end 1760 of the dielectric barrier 1704 to peel the dielectric barrier 1704 away from the electrode 1703 and the substance reservoir 1752, allowing the treatment substance to be applied to the skin. In another embodiment, the electrode 1703 and/or spacers 1708 may be removed along with the dielectric barrier 1704.

Figure 18:
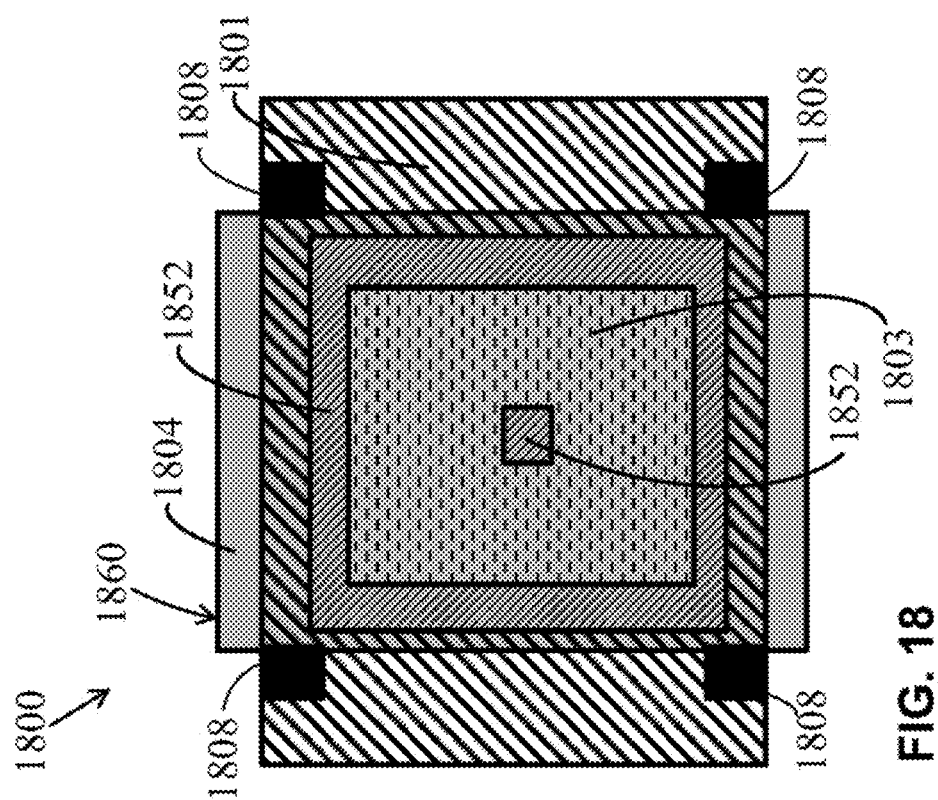
FIG. 18 is a drawing of a bottom view of another exemplary treatment patch with a substance delivery device.

FIG. 18 is a drawing of a bottom view (skin side) of another exemplary treatment patch 1800 with a substance delivery device. Treatment patch 1800 is configured similarly to patch 1600, but with a different arrangement of the electrode and substance reservoir portions. Treatment patch 1800 includes a substrate layer 1801. The substrate layer 1801 may be any material suitable for supporting the other layers and components of the patch 1801, including, for example, connections to other circuits (e.g., power supply, ground, communication signals, etc.) (not shown). Patch 1800 includes a high voltage electrode 1803 and a dielectric barrier 1804 located below the electrode 1803, which are associated with a non-thermal DBD plasma generator. Patch 1800 also includes spacers 1808 to establish the proper gap between the dielectric barrier 1804 and the skin (not shown). The spacers 1808 may be adjustable.

Patch 1800 also includes a treatment substance reservoir 1852. The treatment substance reservoir 1852 is located on top of the electrode 1803 and configured to position an outlet of the substance reservoir 1852 proximate to the skin treatment area. The substance reservoir 1852 holds a treatment substance associated with the skin treatment. In this embodiment, the substance reservoir 1852 is between the substrate layer 1801 and the electrode 1803. In some embodiments, the treatment substance may be encapsulated in a cell placed between the substrate layer 1801 and electrode 1803.

In this embodiment, the dielectric barrier 1804 is removable from the patch 1800. In this manner, the dielectric barrier 1804 functions as the release device for the substance reservoir 1852. In particular, the dielectric barrier 1804 can be removed from the patch 1800 by pulling on a tab end 1860 of the dielectric barrier 1804 to peel the dielectric barrier 1804 away from the electrode 1803 and expose portions of the substance reservoir 1852, allowing the treatment substance to be applied to the skin through the center of the electrode 1803 and around the outside of the electrode 1803. In another embodiment, the electrode 1803 and/or spacers 1808 may be removed along with the dielectric barrier 1804.

Figure 19:
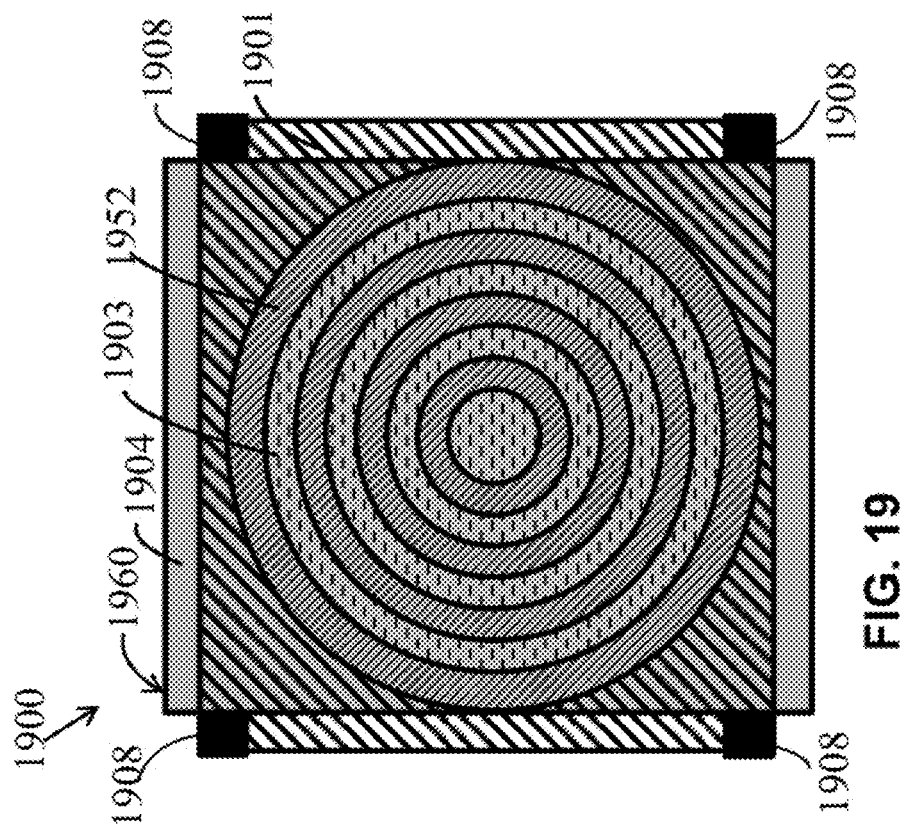
FIG. 19 is a drawing of a bottom view of another exemplary treatment patch with a substance delivery device.

FIG. 19 is a drawing of a bottom view (skin side) of another exemplary treatment patch 1900 with a substance delivery device. Treatment patch 1900 is configured similarly to patch 1800, but with a different arrangement of the electrode and substance reservoir portions. Treatment patch 1900 includes a substrate layer 1901. The substrate layer 1901 may be any material suitable for supporting the other layers and components of the patch 1901, including, for example, connections to other circuits (e.g., power supply, ground, communication signals, etc.) (not shown). Patch 1900 includes high voltage electrodes 1903 and a dielectric barrier 1904 located below the electrodes 1903, which are associated with a non-thermal DBD plasma generator. Patch 1900 also includes spacers 1908 to establish the proper gap between the dielectric barrier 1904 and the skin (not shown). The spacers 1908 may be adjustable.

Patch 1900 also includes treatment substance reservoirs 1952. Rings of the treatment substance reservoirs 1952 are located in between rings of electrodes 1903 and configured with outlets of the substance reservoirs 1952 proximate to the skin treatment area. The substance reservoirs 1952 hold one or more treatment substances associated with the skin treatment. In this embodiment, the substance reservoirs 1952 are located in a space created between the substrate layer 1901 and dielectric barrier 1904, adjacent to the electrodes 1903. In some embodiments, the treatment substance may be encapsulated in a cell placed between the substrate layer 1901 and dielectric barrier 1904.

In this embodiment, the dielectric barrier 1904 is removable from the patch 1900. In this manner, the dielectric barrier 1904 functions as the release device for the substance reservoirs 1952. In particular, the dielectric barrier 1904 can be removed from the patch 1900 by pulling on a tab end 1960 of the dielectric barrier 1904 to peel the dielectric barrier 1904 away from the electrodes 1903 and expose the substance reservoirs 1952, allowing the treatment substance to be applied to the skin. In another embodiment, the electrodes 1903 and/or spacers 1908 may be removed along with the dielectric barrier 1904.

Figure 20:
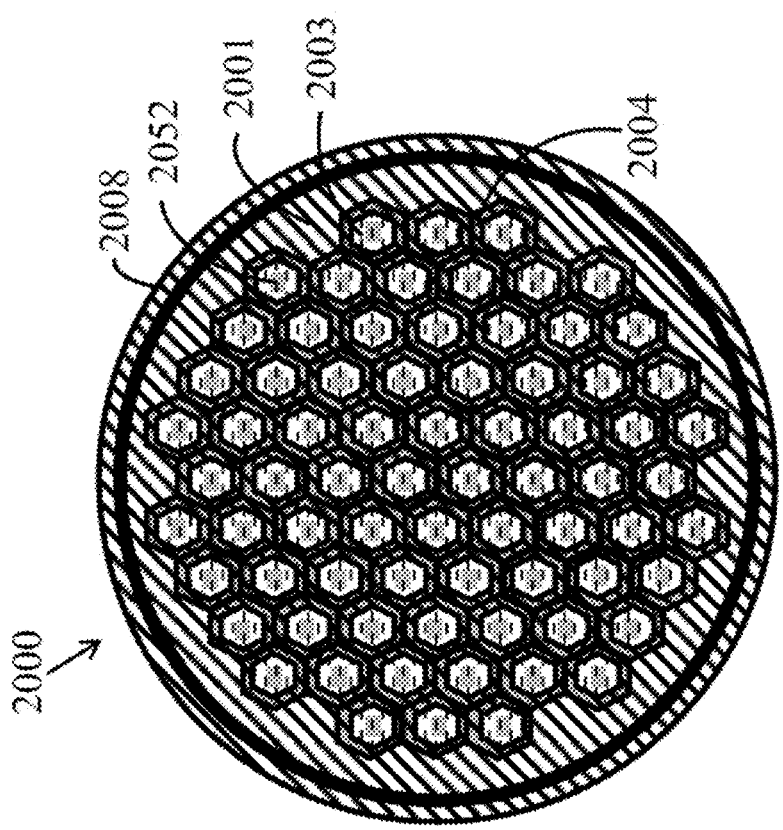
FIG. 20 is a drawing of a bottom view of another exemplary treatment patch with a substance delivery device.

FIG. 20 is a drawing of a bottom view (skin side) of another exemplary treatment patch 2000 with a substance delivery device. Treatment patch 2000 includes a substrate layer 2001. The substrate layer 2001 may be any material suitable for supporting the other layers and components of the patch 2001, including, for example, connections to other circuits (e.g., power supply, ground, communication signals, etc.) (not shown). Patch 2000 includes hexagon-shaped high voltage electrodes 2003 and hexagon-shaped dielectric barriers 2004 located below the electrodes 2003, which are associated with a non-thermal DBD plasma generator. Patch 2000 also includes a ring-shaped spacer 2008 to establish the proper gap between the dielectric barriers 2004 and the skin (not shown). The spacer 2008 encircles the skin treatment area. The spacer 2008 may be adjustable.

Patch 2000 also includes treatment square-shaped substance reservoirs 2052. The treatment substance reservoirs 2052 are located in the center of the electrodes 2003 and configured with outlets of the substance reservoirs 2052 proximate to the skin treatment area. The substance reservoirs 2052 hold one or more treatment substances associated with the skin treatment. In this embodiment, the substance reservoirs 2052 are located in a space created between the substrate layer 2001 and dielectric barrier 2004, adjacent to the electrodes 2003. In some embodiments, the treatment substance may be encapsulated in a cell placed between the substrate layer 2001 and dielectric barrier 2004.

In this embodiment, the dielectric barrier 2004 is removable from the patch 2000. In this manner, the dielectric barrier 2004 functions as the release device for the substance reservoirs 2052. In particular, the dielectric barrier 1904 can be removed from the patch 2000 by peeling the connected dielectric barriers 2004 away from the electrodes 2003 and expose the substance reservoirs 2052, allowing the treatment substance to be applied to the skin. In another embodiment, the electrodes 2003 and/or spacer 2008 may be removed along with the dielectric barriers 2004.

As can be appreciated, any number of configurations of treatment patches can be used for a variety of applications. Various devices, delivery processes, substances, etc., may be more suitable for one configuration versus another.

In other embodiments, the spacers 1608, 1708, 1808, 1908, 2008 also incorporate a conductive element that can connect the skin to circuitry when the conductive elements are in contact with the skin. The circuitry (not shown, described above) associated with the conductive element may be, for example, a grounding circuit. In other embodiments, a separate conductive element may be attached to the skin near the patch 1600, 1700, 1800, 1900, 2000, as discussed above.

In other embodiments, other techniques may be used to expose the treatment substance to the skin using patches 1700, 1800, 1900, 2000, including, for example, creating or exposing a hole in the bottom of the dielectric barrier, removing a thin film covering the substance reservoir, piercing or punching a hole into the dielectric barrier from above the patch (including, e.g., through the substrate layer), squeezing or applying pressure to the patch to rupture the substance reservoir, etc.

In this manner, devices 1200, 1400, 1600, 1700, 1800, 1900, 2000 combine plasmaporation and skin treatment (e.g., transdermal, topical, etc.) drug delivery in a single device. Instead of separately applying plasma to an area of skin and then applying a topical formulation like cream, ointment, devices 1200, 1400, 1600, 1700, 1800, 1900, 2000 combine plasmaporation and drug delivery in a single device to better control the skin treatment process. Exemplary applications for these devices include the application of plasma treatment followed by the administration of drugs through the skin in a medical environment (e.g., a doctor's office, hospital, home use, etc.).

For some drugs, for example, nicotine for smoke cessation, a patch, such as, for example, patches 1600, 1700, 1800, 1900, 2000, may contain the drug and an electrode capable of generating plasma in a single device. In an exemplary embodiment, a user can control the delivery of a substance, such as, for example, nicotine, through the skin at the appropriate dose at predetermined time intervals, for example, as prescribed by a doctor, by simply connecting the patch electrode to a relatively small power source every time the user is scheduled for a dose of the substance (e.g., nicotine). In one embodiment, after every dose, the power supply or controller could have an auto shutoff to prevent over use or over dose of the substance by the user. In other embodiments, a controller associated with the patch, as described below, can communicate with a remote device to monitor compliance, adjust dosages, troubleshoot, etc.

Further integrating grounding elements as a part of the device 1200, 1400, 1600, 1700, 1800, 1900, 2000 enhances the safety of the treatment giver and the patient, especially in a home use environment.

In some embodiments, the substances, including, for example, DNA vaccines, need to be delivered before applying the plasma. In these embodiments, the substance (e.g., DNA vaccine) will be applied either topically or injected intradermally and, after allowing time for diffusion of the substance into the skin to the right depth or immediately after injecting it, then the skin can be treated with plasma to enable intracellular uptake of DNA plasmid. Any of the combination devices 1200, 1400, 1600, 1700, 1800, 1900, 2000 can be configured for providing plasma after delivering the substance in various embodiments.

Figure 21:
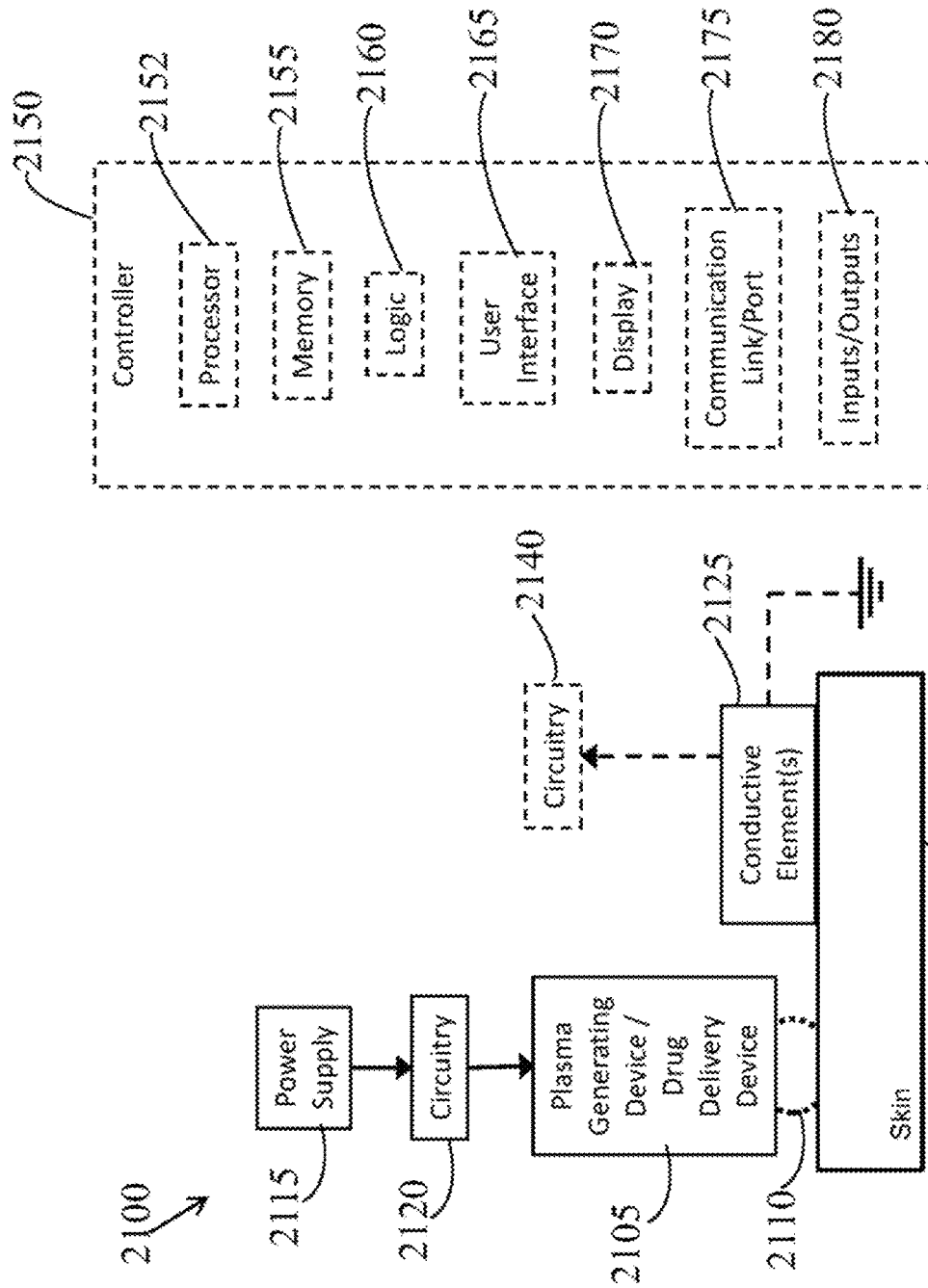
FIG. 21 is block diagram of an exemplary embodiment of a skin treatment apparatus for trans-tissue substance delivery.

FIG. 21 is block diagram of an exemplary embodiment of a skin treatment apparatus 2100 for trans-tissue substance delivery. In this embodiment, the treatment apparatus 2100 includes a plasma generating device 2105 for generating a plasma 2110, a power supply 2115 for powering the plasma generating device 2105, circuitry 2120 for providing one or more electrical pulses to the plasma generating device 2105, and one or more conductive elements 2125 in contact with the skin 2130. In some embodiments, the apparatus 2100 also includes a substance delivery device (not shown), which may be integrated with the plasma generating device 2105. In some embodiments, the power supply 2115 is battery-powered. In various embodiments, the conductive element 2125 is in circuit communication with circuitry 2140. In one embodiment, circuitry 2140 places the conductive element 2125 in circuit communication with ground, including, for example, via other electrical components. In another embodiment, conductive element 2125 is directly grounded. In another embodiment, conductive element 2125 acts as a floating ground. These components of apparatus 2100 can include all of the features mentioned above and discussed in more detail below. These features allow the apparatus to control the creation of a plasma 2110 (and in some embodiments, the delivery of a treatment substance) associated with a skin treatment.

In other embodiments, the apparatus 2100 may include an exemplary controller 2150 for controlling one or more aspects of the apparatus 2100. Controller 2150 may include a processor 2152, a memory 2155, logic 2160, user interface 2165, display 2170, communication link/port 2175, inputs/outputs 2180, and/or any other feature associated with a controller. In one embodiment, the controller 2150 may be embodied as one or more computing devices, such as, for example, a computer (e.g., desktop, laptop, tablet), a portable smart device (e.g., smart phone, programmer, portable controller), etc. In some embodiments, the controller 2150 may be associated with or include an application, detection, and/or quantification module.

Processor 2152 may include a device or combination of devices that function as a processor, as defined above, associated with the skin treatment apparatus or process. Logic 2160 may include software for controlling and/or executing the skin treatment process, timers, process sequences, safety checks, adjustments, dosing, compliance monitoring, etc. The memory 2155 may store the logic 2160, various algorithms associated with the logic 2160, predetermined times/durations for various timed processes, substance dosages, dosage protocols (e.g., alerts, levels, reminders), various settings for the power supply 2115, plasma generating device 2105, circuitry 2120, 2140, etc. The memory 2155 may be of any type or configuration, including, for example, local, remote, permanent, removable, centralized, shared, etc.

The memory 2155 may also store an application database of treatment settings. For example, as apparatus 2100 settings are prescribed, tuned, and/or optimized for various applications, the various application details and associated parameters/settings of the apparatus 2100 can be stored. Exemplary application details may include, for example, the treatment substance (e.g., drug), dosage, skin type, patient tolerance, etc. Exemplary parameters/settings may include, for example, power supply 2115 and associated circuitry 2120 settings (e.g., type, voltage, polarity, waveform, frequency, pulse number and duration, duty cycle, etc.), plasma generating device 2105 settings (plasma type, gas type, flow rate, etc.), spacing (height of plasma generating device 2105 above skin 2130), treatment times/routines, conductive element 2125 features (e.g., placement, shape, size, thickness, material, segments, etc.), circuitry 2140, features (e.g., component (resistor, capacitor, inductor, etc.) values, component arrangement (e.g., series, parallel, etc.), component type (e.g., fixed, variable, etc.), grounding, etc.), etc.

The user interface 2165 may include various input devices, such as, for example, buttons, dials, mouse, keyboard, touch-pad, etc. The display 2170 may include one or more displays, including, for example, monitors, readouts, LCDs, LEDs, etc. The communication link/port 2175 may include various devices suitable for any type of communication, including, for example, network connections (e.g., modem, LAN, WAN), wired (e.g., USB, Ethernet), wireless interfaces (e.g., Bluetooth, 802.11 standards, near field), portable storage medium interfaces (e.g., flash drive ports (e.g., memory sticks, USB, multimedia, SD, compact flash)), etc., including for communication with remote devices and/or stations. Inputs/outputs 2180 may include devices for receiving and/or transmitting various signals, information, readings, etc. associated with the apparatus 2100, including to and/or from various devices, sensors, readouts, etc.

In yet other embodiments, the devices, processes, and/or substances associated with the disclosed skin treatments may be associated with a clinical trial to determine the efficacy and/or effectiveness of particular treatments utilizing the devices, processes, and/or substances. In these embodiments, the apparatus 2100 may communicate with a remote device, such as, for example, an electronic data capture (EDC) and/or clinical trial management system (CTMS), whether in a home or clinical environment. In particular, the apparatus 2100 or controller 2150 can communicate with the remote device to monitor compliance, report outcomes, adjust parameters of the trial (including, for example, device settings (e.g., power, duty cycle, frequency, etc.), process settings (e.g., sequences, steps, times, etc.), substance settings (e.g., types, dosages, etc.)), provide instructions, troubleshoot, store data, exchange messages, etc.

In various embodiments, the various components of apparatus 2100 may be separate components in operative communication with each other or may be integrated to various degrees. The degree of integration may range from discrete components sharing a common housing to full integration into one or more integrated components or devices with combined capabilities.

Figure 22:
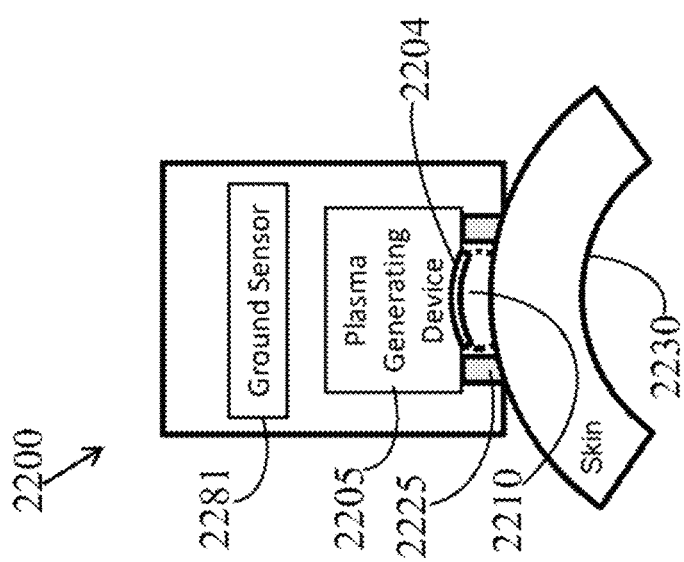
FIG. 22 is a drawing of an exemplary integrated skin treatment apparatus for trans-tissue substance delivery.

For example, as shown in FIG. 22, one embodiment of a skin treatment apparatus 2200 for trans-tissue substance delivery includes a plasma generating device 2205 for generating plasma 2210 between a contoured dielectric 2204 and contoured skin 2230, a spacer/conductive element 2225 in contact with skin 2230, and a ground sensor 2281 integrated into one device. The ground sensor 2281 senses when the skin 2230 is properly grounded via the conductive element 2225.

Figure 23:
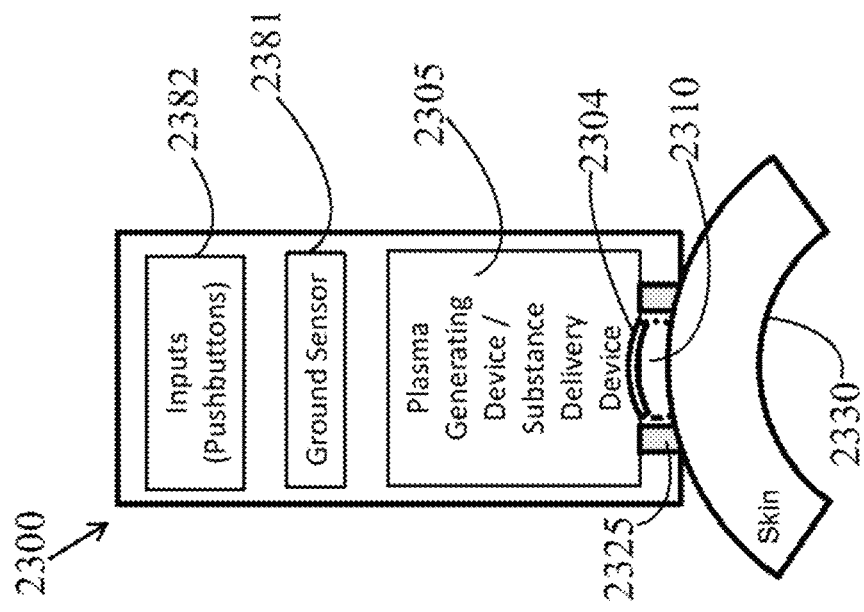
FIG. 23 is a drawing of an exemplary integrated skin treatment apparatus with a substance delivery device.

In another embodiment, as shown in FIG. 23, another embodiment of a skin treatment apparatus 2300 includes a combination plasma generating device/substance delivery device 2305 for generating plasma 2310 and delivering a treatment substance between a contoured dielectric 2304 and contoured skin 2330, a spacer/conductive element 2325 in contact with skin 2330, a ground sensor 2381, and pushbutton inputs 2382 integrated into one device. The ground sensor 2381 senses when the skin 2330 is properly grounded via the conductive element 2325. The pushbutton inputs 2382 are used by a user to initiate the generation of plasma 2310 and initiate the delivery of the treatment substance. In another embodiment, the generation of plasma 2310 and delivery of the treatment substance are automated and controlled by a controller (not shown).

Although FIGS. 22-23 do not show the exemplary controller 2150 and its associated components, any or all of these devices 2150, 2152, 2155, 2160, 2165, 2170, 2175, 2180 may be integrated with any of the components and devices shown in FIGS. 22-23 in other embodiments. As can be appreciated, any number of combinations of devices and features can be integrated into combined devices for skin treatments, including, for example, the components shown in FIG. 21 and described in the various embodiments above.

FIGS. 24-31 are flow diagrams of exemplary methodologies associated with the skin treatment apparatuses. The exemplary methodologies may be carried out in logic, software, hardware, or combinations thereof. In addition, although the methods are presented in an order, the blocks may be performed in different orders. Further, additional steps or fewer steps may be used.

Figure 24:
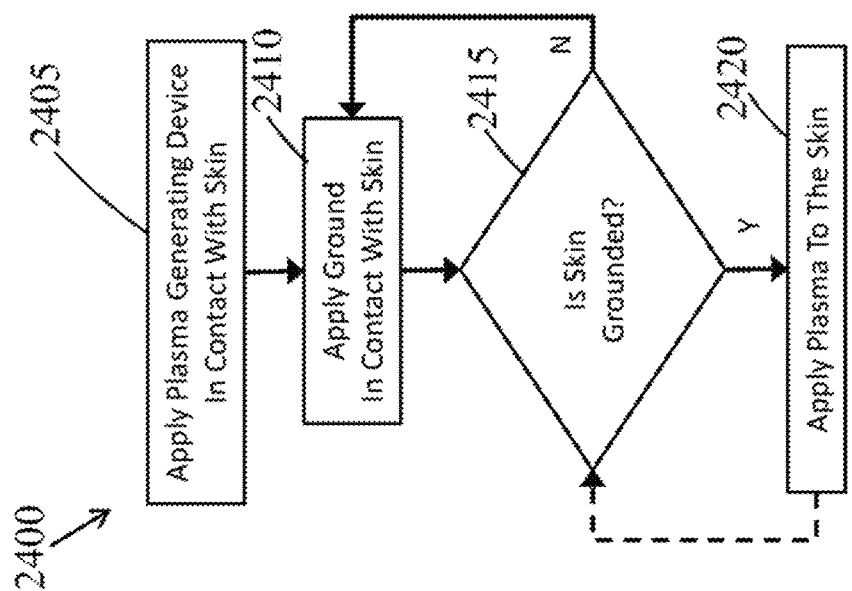
FIG. 24 is a flow diagram of an exemplary method of treating grounded skin with plasma.

FIG. 24 shows an exemplary method 2400 of treating skin using the systems, components, and/or configurations described above. First, at step 2405, the method includes applying a plasma generating device in contact with the skin. Then, at step 2410, the method includes applying a ground in contact with the skin. In this embodiment, the ground is not integrated into the plasma generating device. Next, at step 2415, the method includes determining if the skin is grounded, including, for example, via a position sensor or circuit check. If the skin is grounded, then the method proceeds to step 2420 and applies a plasma to the skin. If the skin is not grounded, then the method returns to step 2410 and continues to look for a ground at step 2415. Plasma is not applied to the skin until the skin is grounded. In another embodiment, the method continues to monitor the ground at step 2415 and can stop applying the plasma to the skin if the ground is interrupted.

Figure 25:
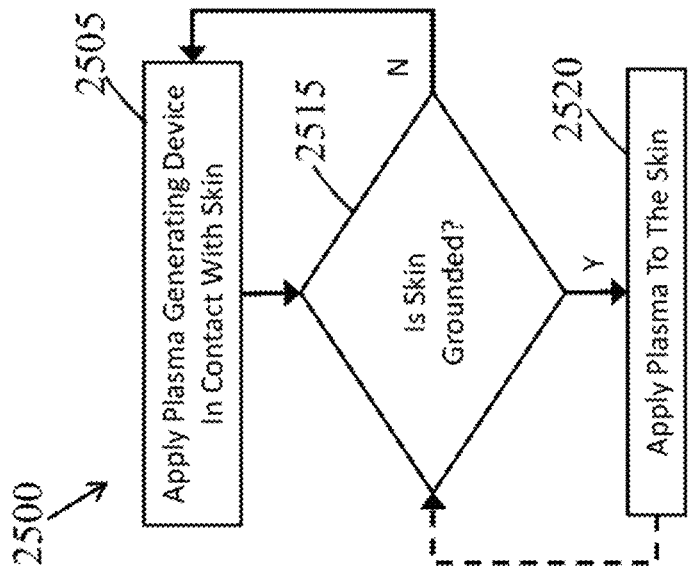
FIG. 25 is a flow diagram of another exemplary method of treating grounded skin with plasma.

FIG. 25 shows another exemplary method 2500 of treating skin using the systems, components, and/or configurations described above. First, at step 2505, the method includes applying a plasma generating device in contact with the skin. In this embodiment, the ground is integrated into the plasma generating device. Next, at step 2515, the method includes determining if the skin is grounded, including, for example, via a position sensor or circuit check. If the skin is grounded, then the method proceeds to step 2520 and applies a plasma to the skin. If the skin is not grounded, then the method returns to step 2505 and continues to look for a ground at step 2515. Plasma is not applied to the skin until the skin is grounded. In another embodiment, the method continues to monitor the ground at step 2515 and can stop applying the plasma to the skin if the ground is interrupted.

FIG. 26 shows another exemplary method 2600 of treating skin using the systems, components, and/or configurations described above. The first three steps, 2605, 2615, and 2620 are the same as steps 2505, 2515, and 2520 of method 2500. At step 2625, the method includes applying a treatment substance to the skin after applying the plasma to the skin.

In other embodiments, a treatment substance can be applied to the skin before applying the plasma generating device in contact with the skin and/or before applying the plasma to the skin.

FIG. 27 shows another exemplary method 2700 of treating skin using the systems, components, and/or configurations described above. The first four steps, 2705, 2715, 2720, and 2725 are the same as steps 2605, 2615, 2620, and 2625 of method 2600. At step 2730, the method includes applying a plasma generating device in contact with the skin again. Next, at step 2735, the method includes determining if the skin is grounded again. If the skin is grounded, then the method proceeds to step 2740 and applies a plasma to the skin again. If the skin is not grounded, then the method returns to step 2730 and continues to look for a ground at step 2735. Plasma is not applied to the skin until the skin is grounded again. In another embodiment, the method continues to monitor the ground at step 2735 and can stop applying the plasma to the skin if the ground is interrupted.

Figure 28:
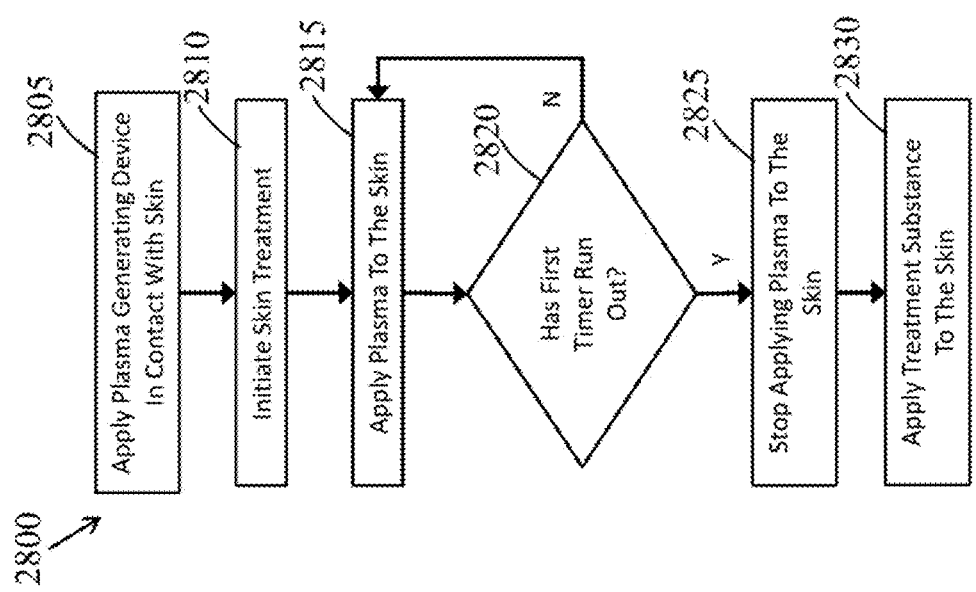
FIG. 28 is a flow diagram of an exemplary method of treating skin with timed plasma application.

FIG. 28 shows an exemplary method 2800 of treating skin using the systems, components, and/or configurations described above. First, at step 2805, the method includes applying a plasma generating device in contact with the skin. Then, at step 2810, the method includes initiating an automatic skin treatment. In one embodiment, a first control button may be used to initiate the skin treatment. For example, an electronic signal may be sent from the button to the plasma generating device, an electronic signal may be sent from the button to a controller that sends another electronic signal to the plasma generating device, etc. Next, at step 2815, the method includes applying a plasma to the skin for a first predetermined duration. In this embodiment, step 2815 includes starting a first timer for the first predetermined duration. At step 2820, the method includes determining if the first timer has run out. If the first timer has not run out, then the method returns to step 2815, continues to apply the plasma, and continues to monitor the first timer at step 2820. If the first timer has run out, then the method proceeds to step 2825 and stops applying the plasma to the skin. At step 2830, the method includes applying a treatment substance to the skin after applying the plasma to the skin. In this manner, the plasma is automatically applied for a predetermined duration after the skin treatment is initiated by a user. In other embodiments, the treatment substance can be applied to the skin before applying the plasma generating device in contact with the skin and/or before applying the plasma to the skin.

Figure 29:
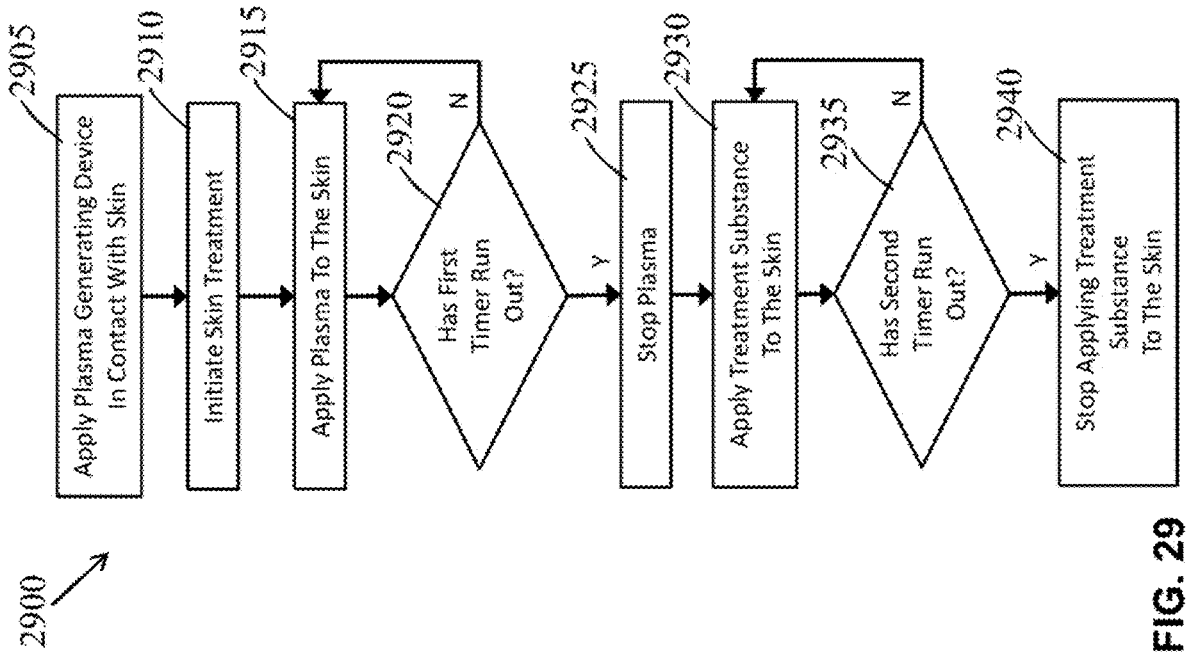
FIG. 29 is a flow diagram of another exemplary method of treating skin with timed plasma and substance application.

FIG. 29 shows an exemplary method 2900 of treating skin using the systems, components, and/or configurations described above. The first five steps, 2905, 2910, 2915, 2920, and 2925 are the same as steps 2805, 2810, 2815, 2820, and 2825 of method 2800. Next, at step 2930, the method includes applying a treatment substance to the skin for a second predetermined duration. In this embodiment, step 2930 includes starting a timer for the second predetermined duration. In this embodiment, applying the treatment substance to the skin is part of the automatic skin treatment initiated at step 2910. For example, an electronic signal may be sent from the button to the plasma generating device and a substance release device, an electronic signal may be sent from the button to a controller that sends another electronic signal to the plasma generating device and the substance release device, etc. In another embodiment, the first control button may be used to initiate the plasma application and a second control button (or a second actuation of the first control button) may be used to initiate applying the treatment substance. For example, an electronic signal may sent from the button to a substance release device, an electronic signal may sent from the button to a controller that sends another electronic signal to the substance release device, etc.

Continuing with method 2900, at step 2935, the method includes determining if the second timer has run out. If the second timer has not run out, then the method returns to step 2930, continues to apply the treatment substance, and continues to monitor the second timer at step 2935. If the first timer has run out, then the method proceeds to step 2940 and stops applying the treatment substance to the skin. For example, stopping the application of the treatment substance to the skin may include, for example, stopping the release of the treatment substance, wiping away any excess treatment substance from the surface of the skin, etc. In this manner, the plasma and treatment substance are automatically applied during separate predetermined durations after the skin treatment is initiated by a user. In other embodiments, the treatment substance can be applied to the skin before applying the plasma to the skin.

Figures 30, 31:
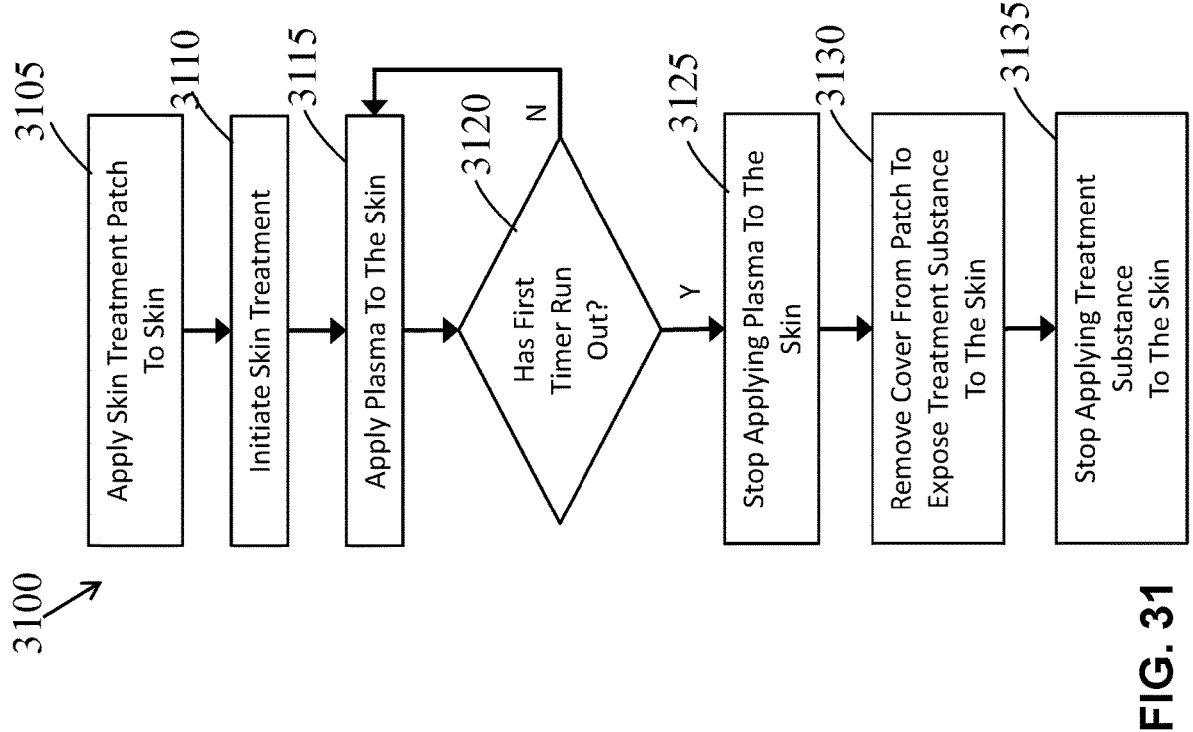
FIG. 30 is a flow diagram of an exemplary method of treating skin with a treatment patch.
FIG. 31 is a flow diagram of an exemplary method of treating skin with a treatment patch.

FIG. 30 shows another exemplary method 3000 of treating skin using the systems, components, and/or configurations described above. First, at step 3005, the method includes applying a skin treatment patch in contact with the skin. In further embodiments, a separate ground may be applied to the skin or a ground may be integrated into the patch and simultaneously applied in contact with the skin, including, for example, via conductive spacers. In these embodiments, the method may also include determining if the skin is grounded, including, for example, via a circuit check. Next, the method proceeds to step 3010 and applies a plasma to the skin. At step 3015, the method includes removing a cover from the patch to expose a treatment substance to the skin. In some embodiments, the cover includes the dielectric barrier, electrode, and/or spacers associated with the plasma generating device of the patch. In some embodiments, removing the cover may include, for example, pulling a tab of the cover from the side of the patch (while optionally applying pressure to the top of the patch to maintain contact with the skin), slightly lifting a portion of the patch to allow for removal of the cover from the bottom, etc. Finally, at step 3020, the method includes removing the patch from the skin after applying the treatment substance for a prescribed time duration (which may be monitored with a timer, including, for example, a timer associated with a controller of the system) and/or until a sufficient dose of the treatment substance is delivered.

FIG. 31 shows another exemplary method 3100 of treating skin using the systems, components, and/or configurations described above. First, at step 3105, the method includes applying a skin treatment patch in contact with the skin. In further embodiments, a ground and/or ground check may also be incorporated as described above in method 3000 of FIG. 30. Then, at step 3110, the method includes initiating an automatic skin treatment. In one embodiment, a first control button may be used to initiate the skin treatment. For example, an electronic signal may be sent from the button to the plasma generating device, an electronic signal may be sent from the button to a controller that sends another electronic signal to the plasma generating device, etc. Next, at step 3115, the method includes applying a plasma to the skin for a first predetermined duration. In this embodiment, step 3115 includes starting a first timer for the first predetermined duration (e.g., a timer associated with a controller of the system). At step 3120, the method includes determining if the first timer has run out. If the first timer has not run out, then the method returns to step 3115, continues to apply the plasma, and continues to monitor the first timer at step 3120. If the first timer has run out, then the method proceeds to step 3125 and stops applying the plasma to the skin. At step 3130, the method includes removing a cover from the patch to expose a treatment substance to the skin. In some embodiments, the cover includes the dielectric barrier, electrode, and/or spacers associated with the plasma generating device of the patch. Finally, at step 3135, the method includes removing the patch from the skin after applying the treatment substance for a prescribed time duration (which may be monitored with another timer, including, e.g., a timer associated with the controller of the system) and/or until a sufficient dose of the treatment substance is delivered.

Any of the aforementioned methods or steps may be combined. For example, in other embodiments, the ground monitoring steps associated with methods 2400, 2500, 2600, 2700 may be combined with methods 2800, 2900, 3000, 3100.

Other types of plasma generators may be used for skin treatment systems, such as, for example, nanosecond pulsed DBD plasma, microsecond pulsed DBD plasma, sinusoidal DBD plasma, corona discharge, glow discharge, resistive barrier discharge plasma, surface DBD plasma, a floating-electrode DBD plasma generator that generates a plasma jet, 2-D or 3-D array of DBD plasma jets operating under a continuous mode or under a controlled duty cycle ranging from 1-100% and the like. Plasma jets utilize a gas feed. Exemplary gases that may be used to feed the plasma jet include air, He, He+$O_2$, $N_2$, He+$N_2$, Ar, Ar+$O_2$, Ar+$N_2$, and the like. Gases resulting from the evaporation of liquid solutions can also be used. Examples of vaporized liquids may include water, ethanol, organic solvents and the like. These vaporized liquids may be mixed with additive compounds. The evaporated liquids and additives may be used with the gases identified above in various concentrations or without the gases. During operation, the plasma jet is in direct contact with the skin.

It is important to note that not all plasma generators may be used to successfully induce poration. Thermal plasmas, gliding arc discharges, DC hollow cathode discharge, and plasmatron generators are examples of plasma generators that are not suitable for use in plasmaporation. Such plasma generators either deliver conduction current, which causes thermal damage, muscle contraction and pain or do not deliver sufficient charges to the substrate being treated, which would mean no or very weak applied electric field and hence no induced poration.

Suitable plasma generators have dominating currents that are displacement currents at low power and/or high frequencies. Displacement current has units of electric current density, and an associated magnetic field just as conduction current has, however, it is not an electric current of moving charges, but rather a time-varying electric field. The electric field is applied to the skin by an insulated high-voltage electrode that is not in contact with the skin. Because this electrode is insulated and is not in contact with the skin, there is no flow of conduction current into the skin, which would cause thermal damage, muscle contraction and pain that is associated with electroporation.

For larger treatment areas, electrode configurations consisting of multiple plasma jets or larger area flat electrodes may be used. In the case of more complex 3D surfaces, a controlled plasma module may move around a stationary target or the surface to be exposed to the plasma may be placed on a movable stage. In some embodiments, one or more plasma jets or can be attached to a robotic arm that is programmed to move in a manner that exposes one or more target areas to a plasma plume or jet.

In addition, in some embodiments, the plasma generator may be coupled with a biomolecule/drug delivery system, where molecules may be transported to the treatment area through needle-free injection, evaporation, spraying and or misting. In some embodiments, this may assist with the pretreatment of the surface.

In some embodiments where it is essential to reduce the plasma temperature and enhance skin permeation following plasmaporation it is beneficial to generate non-thermal plasma using He, Ar, Ne, Xe and the like, air, or mixtures of inert gases with small percentage (0.5%-20%) of other gases such as $O_2$ and $N_2$ and mixtures of inert gases with vaporized liquids including water, DMSO, ethanol, isopropyl alcohol, n-butanol, with or without additives and the like.

Although the embodiments described herein are described with respect to skin, the inventive concepts described herein are applicable to other tissue or organs. In addition, while certain substances (e.g., molecules, drugs, and vaccines) have been mentioned, the exemplary systems and methods described herein are applicable to many other substances, including, for example, DNA vaccines, to application of growth factors, antitumor drugs, chemotherapeutic drugs, immunomodulating drugs, particles and the like where it may be desirable to move the substance or item between cells, such as those in the stratum corneum and/or into cells, such as those in the epidermis or dermis.

Although many of the exemplary methods above relate to molecules, particles having similar molecular weights or equivalent diameters may also be transported across layers of the skin. In some embodiments, nanoparticles, such as, for example, silver nanoparticles, silver ions and other metal or polymer nanoparticles are driven into pores in the skin where they are allowed to react. Silver, copper and other metals are known to induce cell lysis and inhibit cell transduction. The introduction of silver and other metals in the form of nanoparticles increases the surface area available to react with microorganisms and enhances the antimicrobial action. Additionally, introduction of nanoparticles that encapsulate the molecule, vaccine, or drug of interest after plasmaporation allows permeation of such molecules to a controlled depth leading to controlled long term release of actives within a particular area of skin. Nanoparticles, including quantum dots, nanotubes and the like, having a diameter of between about 2 and about 400 nanometers may be driven across the skin using plasmaporation.

While the exemplary embodiments are illustrated using skin, any of the described embodiments would work equally well with any tissue, including, for example, epithelial tissue; mucosal epithelial tissue; muscle tissue; connective tissue; and inner and outer lining of organs.

While the present invention has been illustrated by the description of embodiments thereof and while the embodiments have been described in considerable detail, it is not the intention of the applicant to restrict or in any way limit the scope of the appended claims to such detail. Additional advantages and modifications will readily appear to those skilled in the art. Therefore, the invention, in its broader aspects, is not limited to the specific details, the representative apparatus and methods, and illustrative examples shown and described. Accordingly, departures may be made from such details without departing from the spirit or scope of the applicant's general inventive concept. While the embodiments discussed herein have been related to the systems and methods discussed above, these embodiments are intended to be exemplary and are not intended to limit the applicability of these embodiments to only those discussions set forth herein. The control systems and methodologies discussed herein may be equally applicable to, and can be utilized in, other systems and methods.

We claim:

1. A method of treating skin comprising:
applying a treatment substance to skin associated with a skin treatment, wherein a treatment patch comprises:
a substrate that flexibly conforms to a shape of the skin; and
a substance reservoir for holding the treatment substance associated with the skin treatment;
generating a plasma; and
exposing the skin associated with the skin treatment to the plasma and the treatment substance during the skin treatment.

2. The method of claim 1, wherein the treatment patch comprises a cover over the treatment substance and the method further comprises removing the cover to expose the treatment substance to the skin.

3. The method of claim 2, wherein the cover comprises a dielectric barrier for preventing a high voltage electrode of a plasma generating device from contacting the skin when exposing the skin to the plasma.

4. The method of claim 1, wherein the treatment patch further comprises at least one of a high voltage electrode for creating the plasma above the skin, a dielectric barrier for preventing the high voltage electrode of the plasma generating device from contacting the skin, and at least one spacer for providing a gap between the dielectric barrier and the skin surface.

5. The method of claim 4, wherein the treatment patch comprises a cover over the treatment substance and wherein removing the cover comprises removing at least one of the high voltage electrode, the dielectric barrier, and the at least one spacer from the treatment patch.

6. The method of claim 1, wherein exposing the skin to the plasma comprises porating the skin.

7. The method of claim 1, wherein exposing the skin associated with the skin treatment to the plasma and the treatment substance during the skin treatment comprises applying the treatment substance to the skin after applying the plasma to the skin.

8. The method of claim 1, wherein exposing the skin associated with the skin treatment to the plasma and the treatment substance during the skin treatment comprises applying the plasma to the skin after applying the treatment substance to the skin.

9. The method of claim 1, wherein the skin treatment increases the speed of permeation of the treatment substance into the skin.

10. The method of claim 1, wherein exposing the skin to the plasma comprises generating the plasma for a first predetermined duration, exposing the skin to the treatment substance comprises then exposing the skin to the treatment substance for a second predetermined duration, and exposing the skin to the plasma further comprises then generating the plasma for a third predetermined duration.

11. The method of claim 1, further comprising:
determining if the skin is grounded; and
exposing the skin to the plasma if the skin is grounded.

12. The method of claim 1, wherein exposing the skin to the treatment substance comprises applying the treatment substance to the skin through a hole in an electrode associated with generating the plasma.

13. The method of claim 1, wherein exposing the skin to the treatment substance comprises applying the treatment substance to the skin through a hole in a dielectric barrier for preventing an electrode of the plasma generating device from contacting the skin.

14. The method of claim 1, wherein the treatment patch further comprises microneedles to porate the skin or deliver the treatment substance to the skin.

15. The method of claim 1, wherein the treatment patch comprises at least one connection to an electrical circuit.

16. The method of claim 15, wherein the electrical circuit comprises a grounding path.

17. A method of treating skin comprising:
generating a plasma;
applying a treatment substance to skin associated with a skin treatment, wherein a substance delivery device comprises a substance reservoir for holding the treatment substance associated with the skin treatment; wherein the substance delivery device comprises a treatment patch that flexibly conforms to a shape of the skin during the skin treatment; and
exposing the skin associated with the skin treatment to the plasma and the treatment substance during the skin treatment.

18. The method of claim 17, wherein the treatment patch comprises microneedles to porate the skin or deliver the treatment substance to the skin.

19. The method of claim 17, wherein applying the treatment substance to the skin associated with the skin treatment comprises delivering the treatment substance from the substance reservoir through a needle to the skin.

* * * * *